(12) United States Patent
Siegal et al.

(10) Patent No.: US 7,179,447 B1
(45) Date of Patent: Feb. 20, 2007

(54) TYPE I INTERFERON-PRODUCING CELLS AND USES THEREOF

(75) Inventors: Frederick P. Siegal, New York, NY (US); Michael Shodell, New York, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 10/067,146

(22) Filed: Feb. 4, 2002

Related U.S. Application Data

(63) Continuation of application No. 09/591,223, filed on Jun. 9, 2000, now abandoned.

(60) Provisional application No. 60/138,619, filed on Jun. 11, 1999.

(51) Int. Cl.
| A61K 49/00 | (2006.01) |
| A61K 35/12 | (2006.01) |
| A61K 35/14 | (2006.01) |
| C12Q 1/00  | (2006.01) |
| G01N 33/53 | (2006.01) |
| G01N 33/567| (2006.01) |

(52) U.S. Cl. .............. 424/9.1; 435/4; 435/7.1; 435/7.2; 435/7.21; 424/9.2; 424/520; 424/529; 424/534

(58) Field of Classification Search .............. 435/4, 435/7.1, 7.2, 7.21, 7.24; 424/9.1, 184, 529, 424/534
See application file for complete search history.

(56) References Cited

U.S. PATENT DOCUMENTS 5,676,942 A    10/1997 Testa et al.

OTHER PUBLICATIONS

Shodell et al Scan. J. Immunol 56:518-521, 2002.*
Schmidt et al. Variations in Plasmacytoid Dendritic Cell (PDC) and Myeloid Dendritic Cell (MDC) Levels in HIV-Infected Subjects on and off Antiretroviral Therapy. J Clin Immunol. 26(1):55-64, 2006.*
Finke et al.Dendritic cell numbers in the blood of HIV-1 infected patients before and after changes in antiretroviral therapy. J Clin Immunol. 24(6):647-52, 2004.*
Abb et al., 1983, "Phenotype of human alpha-interferon producing leucocytes identified by monoclonal antibodies," Clin Exp Immunol. 52(1):179-84.
Autran et al., 1997, "Positive effects of combined antiretroviral therapy on CD4+ T cell homeostasis and function in advanced HIV disease," Science 277(5322):112-6.
Bandyopadhyay et al., 1986, "Requirement for HLA-DR+ accessory cells in natural killing of cytomegalovirus-infected fibroblasts," J Exp Med. 164(1):180-95.
Brinkmann et al., 1993, "Interferon alpha increases the frequency of interferon gamma-producing human CD4+ T cells," J Exp Med. 178(5):1655-63.
Bubenik, 1996, "Cytokine Gene-Modified Vaccines in the Therapy of Cancer," Pharmacol. Ther. 69(1):1-14.
Cederblad et al., 1991, "Interferons and the colony-stimulating factors IL-3 and GM-CSF enhance the IFN-alpha response in human blood leucocytes induced by herpes simplex virus," Scand J Immunol. Nov. 1991;34(5):549-55.
Chehimi et al., 1989, "Dendritic cells and IFN-alpha-producing cells are two functionally distinct non-B, non-monocytic HLA-DR+ cell subsets in human peripheral blood," Immunology 68(4):488-90.
Clerici et al., 1994, "The Th1-Th2 hypothesis of HIV infection: new insights," Immunol Today 15(12):575-81 Review.
Dong et al., 1999, Cancer Res. 59:872-879.
Eck et al., 1996, "Gene-Based Therapy," Pharmacological Basis of Therapeutics, Chapter 5: 77-101.
Empson et al., 1999, "Atopy, anergic status, and cytokine expression in HIV-infected subjects," J Allergy Clin Immunol. 103(5 Pt 1):833-42.
Feldman et al., 1995, J. Leuk. Biol. 57:214-220.
Feldman et al., 1994, Virology 204:1-7.
Feldman et al., 1990, J. Interferon Res. 10:435-446.
Ferbas et al., 1995, Clin. Diagn. Lab. Immunol. 2:138-142.
Ferbas et al., 1994, J. Immunol. 152:4649-4662.
Fitzgerald-Bocarsly, 1993, Pharmacol. Ther. 60:39-62.
Fitzgerald-Bocarsly, 1988, J. Leuk. Biol. 43:323-334.
Ghanekar et al., 1996, J. Immunol. 157:4028-4036.
Grourard et al., 1997, J. Exp. Med. 185:1101-1111 (or Grouard).
Harrison et al., 1997, J.. Immunol. 158:459-463.
Howell et al., 1994, Clin. Immunol. Immunopathol. 71(2):223-230.
Isaacs et al.l, 1957, Proc. R. Soc. London 147:25B.
Kirchner et al., 1979, Immunobiology 156:65-75.
Komanduri et al., 1998, Nat. Med. 4:953-956.

(Continued)

*Primary Examiner*—Sumesh Kaushal
(74) *Attorney, Agent, or Firm*—Amster Rothstein & Ebenstein LLP

(57) ABSTRACT

The present invention provides compositions for the treatment, inhibition or prevention of diseases or disorders, including cancer, immune diseases or disorders, and infectious diseases, comprising interferon-producing cells (IPCs) and methods of administering the IPCs. The present invention also provides compositions for the treatment, inhibition or prevention of diseases or disorders, including cancer, immune diseases or disorders, and infectious disease, comprising purified interferon (IFN) from IPCs and methods of administering the IFN. The present invention further provides methods for monitoring the progression of a disease or a disorder such as HIV infection or cancer, comprising measuring the abundance of IPCs in lymphoid organs or blood samples from a subject suffering from a disease or disorder.

15 Claims, 7 Drawing Sheets

OTHER PUBLICATIONS

Figure 1:
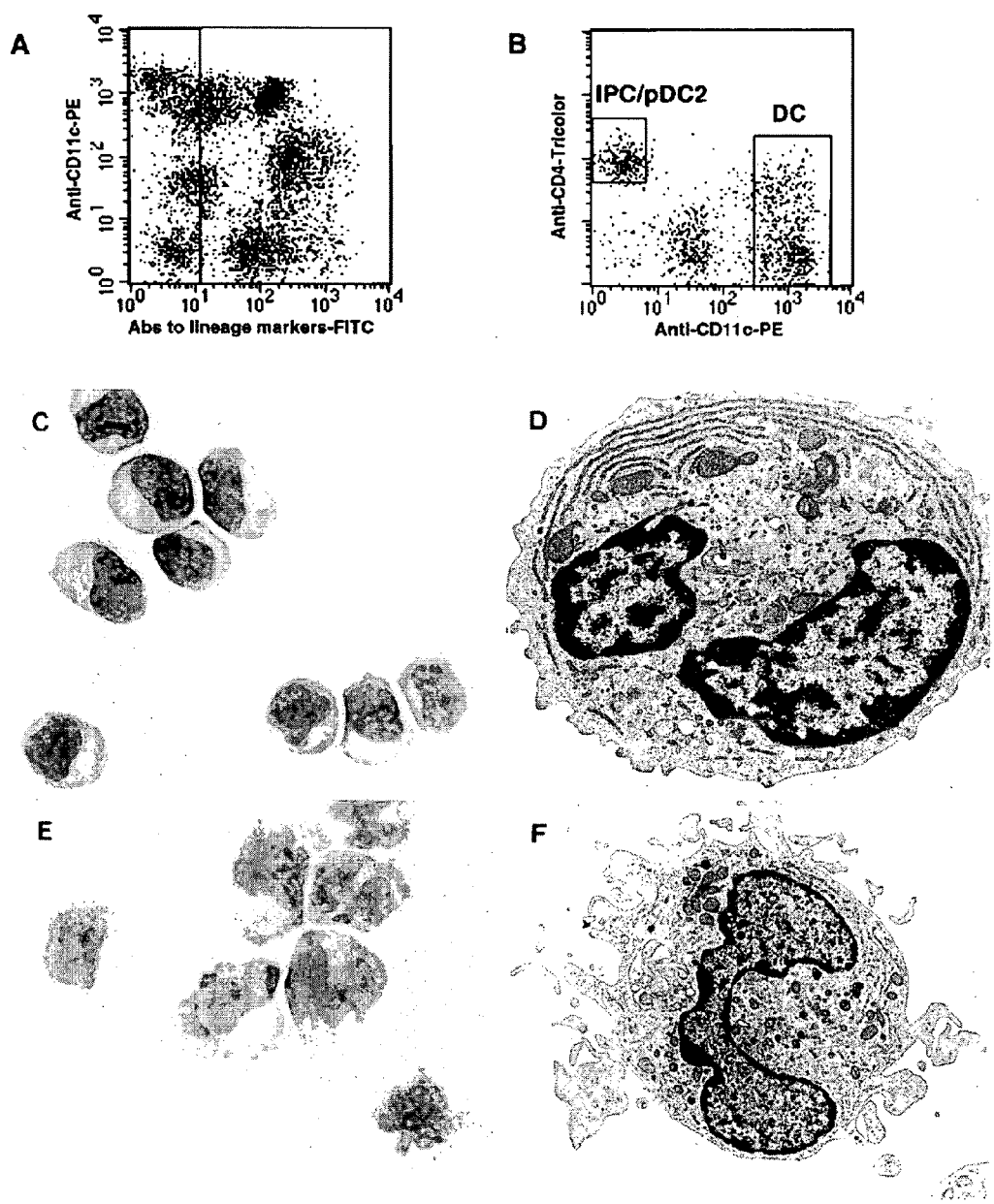

Kostense et al., 1998, AIDS 12:F235-240.
Ledergerber et al., 1999, J. Amer. Med. Assn. 282:2220-2226.
Lederman et al., 1998, J. Inf. Dis. 178:70-79.
Ledley, 1991, Human Gene Therapy 2:77-83.
Leigh et al., 1998, J. Acquir. Immune Ded. Syndr. Hum. Retrovirol. 19:373-380.
Lopez et al., 1983, J. Inf. Dis. 148:962-966.
Marrack et al., 1999, J. Exp. Med. 189:52.
Milone et al., 1998, J. Immunol. 161:2391-2399.
Mocroft et al., 1998, Lancet 352:1725-1730.
O'Doherty et al., 1994, Immunology 82:487.
O'Doherty et al., 1993, J. Exp. Med. 178:1067.
Olweus et al., 1997, PNAS USA 94:125551.
Pakker et al., 1998, Nat. Med. 4:208-214.
Palella et al., 1998, N. Engl. J. Med. 338:853-860.
Parronchi et al., 1996, Eur. J. Immunol. 26:697-703.
Payvandi et al., 1998, J. Immunol. 160:5861-5868.
Perussia et al., 1985, Nat. Immunol. Cell Growth Regul. 4:120-137.
Peter et al., 1980, Eur. J. Immunol. 10:547-555.
Pontesilli et al., 1999, Immunol. Lett. 66:213-217.
Powderly et al., 1998, J. Amer. Med. Assoc. 280:72-77.
Qin et al., 1998, PNAS 95:14411-14416.
Rappocciolo et al., 1989, J. Clin. Microbiol. 27:41-48.
Rissoan et al., 1999, science 283:1183-1186.
Rogge et al., 1998, J. Immunol. 161:6567-6574.
Sandberg et al., 1991, Scan. J. Immunol. 34:565-576.
Sandberg et al., 1990, J. Immunol. 145:1015-1020.
Sanhadji et al., 1997, AIDS 11:977-986.
Schneider et al., 1999, Lancet 353:201-203.
Shodell, M., FP Siegal: abstract submitted, FASEB AAI/CIS Congress, Seattle, WA, May, 2000.
Siegal et al., 1999, Science 284:1835-1837.
Siegel et al., 1994, Leukemia 8:1474-1479.
Siegal et al., 1986, J. Clin. Invest. 78:115-123.
Starr et al., 1993, Acv. Exp. Med. Biol. 329:173-178.
Sun et al., 1998, J. Exp. Med. 188:2335.
Svensson et al., 1996, J. Interferon Cytok. Res. 16:7-16.
Svensson et al., 1996, Scan. J. Immunol. 44:164-172.
Viellard et al., 1997, PNAS 94:11595-11600.

* cited by examiner

Replacement Sheet
FIG. 2
A
B
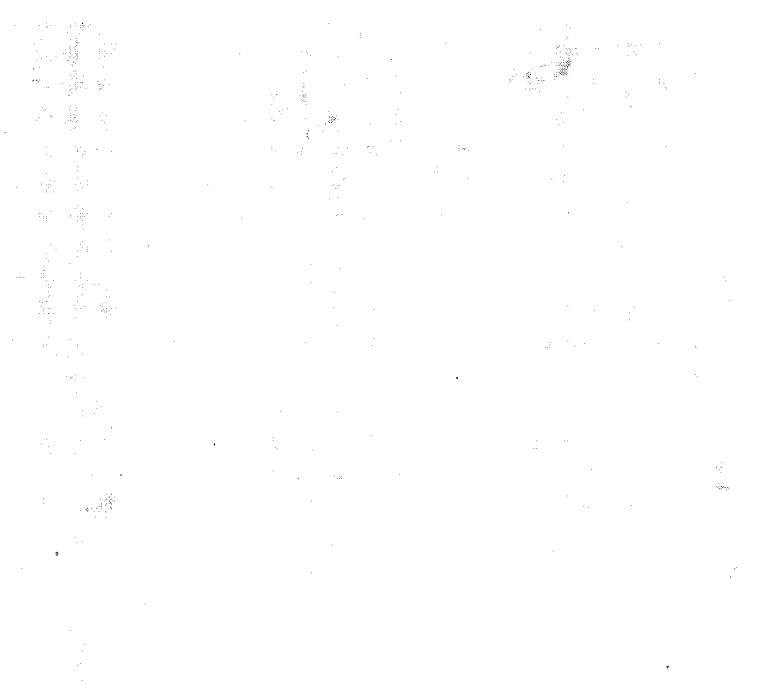

MONTHS AFTER LAST DETECTABLE VIREMIA

US 7,179,447 B1

TYPE I INTERFERON-PRODUCING CELLS AND USES THEREOF

This is a continuation of U.S. patent application Ser. No. 09/591,223, filed Jun. 9, 2000 now abandoned, which claims priority under 35 U.S.C. § 119(e) to U.S. provisional patent application Ser. No. 60/138,619, filed Jun. 11, 1999, each of which is incorporated herein by reference in its entirety.

1. INTRODUCTION

The present invention relates to therapeutic compositions for the treatment, prevention or inhibition of diseases or disorders, comprising administering type I interferon-producing cells. The present invention also relates to methods of administering interferon-producing cells for the treatment, prevention or inhibition. The invention further relates to methods of monitoring the progression of diseases and disorders comprising measuring the number of type I interferon-producing cells.

2. BACKGROUND OF THE INVENTION

2.1. Interferon-Producing Cells

Interferons (IFNs) were discovered in the 1950s as factors rapidly produced by virus-infected cells that enable neighboring cells to resist virus infection (Issacs et al., 1957, Proc. R. Soc. London 147: 25B). IFN-α (leukocyte IFN) and IFN-β (fibrosis IFN), the two type 1 antiviral IFNs, are distinct from type 2 IFN-γ produced by effector T cells. Type 1 IFNs have pleiotropic effects on the immune system, including up-regulation of major histocompatibility complex (MHC) class I on all cell types and activation of macrophage and NK cells (Fitzgerald-Bocarsly, 1993, Pharmacol. Ther. 60: 39). IFNs are also critical in the activation and survival of both $CD4^+$ and $CD8^+$ T cells (Sun et al., 1998, J. Exp. Med 188: 2335; Marrack et al., 1999, J. Exp. Med 189: 52).

Specialized leukocytes, the "natural IFN-producing cells", were shown to be the chief IFN-α producers in response to enveloped viruses, bacteria, and humoral cells (Fitzgerald-Bocarsly, 1993, Pharmacol. Ther. 60: 39; Kirchner et al., 1979, Immunobiology 156: 65; Peter et al., Eur. J. Immunol. 10: 547; Abb et al., Clin Exp. Immunol. 52: 179; Perussia et al., 1985, Nat. Immun. Cell Growth Regul. 4: 120; Chehlml et al., 1989, Immunology 68: 488; Sandberg et al., 1991, Scan. J. Immunol. 34: 565; Starr et al., 1993, Acv. Exp. Med. Biol. 329: 173; Svensson et al., 1996, Scan. J. Immunol. 44: 164; Feldman et al., 1994, Virology 204: 1; Feldman et al., 1990, J. Interferon Res. 10: 435; Perbas et al., 1995, J. Leukocyte Biol. 57: 214; Ghanekar et al., 1996, J. Immunol. 157: 4028). These specialized leukocytes have been shown to express CD4 and MHC class II, but lack hematopoietic-lineage markers (Fitzgerald-Bocarsly, 1993, Pharmacol. Ther. 60: 39; Kirchner et al., 1979, Immunobiology 156: 65; Peter et al., Eur. J. Immunol. 10: 547; Abb et al., Clin Exp. Immunol. 52: 179; Perussia et al., 1985, Nat. Immun. Cell Growth Regul. 4: 120; Chehlml et al., 1989, Immunology 68: 488; Sandberg et al., 1991, Scan. J. Immunol. 34: 565; Starr et al., 1993, Acv. Exp. Med. Biol. 329: 173; Svensson et al., 1996, Scan. J. Immunol. 44: 164; Feldman et al., 1994, Virology 204: 1; Feldman et al., 1990, J. Interferon Res. 10: 435; Ferbas et al., 1995, J. Leukocyte Biol. 57: 214; Ghanekar et al., 1996, J. Immunol. 157: 4028). The nature of these specialized leukocytes has been controversial. In particular, it has been controversial in the art as to whether the specialized leukocytes represent dendritic cells (Perussia et al., 1985, Nat. Immun. Ce. Growth Regul. 4: 120; Feldman et al., 1990, J. Interferon Res. 10: 435; Ghanekar et al., 1996, J. Immunol. 157: 4028) or cells of a distinct lineage (Chehemi et al., 1989, Immunology 68: 488; Starr et al., 1993, Acv. Exp. Med. Biol. 329: 173). The specialized leukocytes have been neither isolated nor further characterized because of their rarity, rapid apoptosis, and lack of lineage markers.

2.2. Type 2 Dendritic Cells

A plasmacytoid cell type from human tonsils and blood that lacks lineage markers also expresses CD4 and MHC class II (O'Doherty et al., 1993, J. Exp. Med. 178: 1067; O'Doherty et al., 1994, Immunology 82: 487; Grouard et al., 1997, J. Exp. Med. 185: 1101; Olweas et al., 1997, Proc. Natl. Acad. Sci. U.S.A. 94: 125551; Rissoan et al., 1999, Science 283: 1183). These cells differentiate into type 2 dendritic cells (DC2s) when cultured with interleukin-3 (IL-3) and CD40 ligand (Grouard et al., 1997, J. Exp. Med. 185: 1101; Rissoan et al., 1999, Science 283: 1183). Unlike monocyte-derived type 1 dendritic cells (DC1s) that induce type 1 T helper cell (TH1) differentiation, DC2s induce type 2 T helper cell (TH2) differentiation (Rissoan et al., 1999, Science 283: 1183).

3. SUMMARY OF THE INVENTION

The present invention provides compositions for the treatment, inhibition or prevention of diseases or disorders, including cancer, immune diseases or disorders, and infectious diseases, comprising interferon-producing cells (IPCs) and methods of administering the IPCs. The present invention also provides methods and compositions for the treatment, inhibition or prevention of diseases or disorders, including cancer, immune diseases or disorders, and infectious disease, comprising purified interferon (IFN) from IPCs and methods of administering the IFN. The present invention further provides methods for monitoring the progression of a disease or a disorder such as HIV infection or cancer, comprising measuring the abundance of IPCs in lymphoid organs or blood samples from a subject suffering from a disease or disorder. The invention is based, in part, on Applicants' discovery that type I interferon-producing cells (IPCs) are type I interferon (IFN) producing cells. The invention is also based on the principle that genetic engineering can be used to improve the properties of cells destined for implantation in vivo, and most importantly, in human subjects.

4. BRIEF DESCRIPTION OF THE DRAWINGS

FIG. 1. Tracing and isolation of IPCs/pDC2s from human peripheral blood. $CD3^+$ T cells, $CD19^+$ B cells, $CD16^+$ and $CD56^+$ NK cells, and $CD14^+$ monocytes were depleted from blood mononuclear cells by immunomagnetic beads (Dynabeads M-450; Dynal, Oslo, Norway). The cells were stained with anti-CD4-Tricolor (Immunotech, Marseille, France), anti-CD11c-PE (Becton Dickinson, San Jose, Calif.), and a mixture of fluorescein isothiocyanate-labeled antibodies to CD3, CD15, CD16, CD20, CD57 (Becton Dickinson), CD14 (coulter, Miami, Fla.), and CD34 (Immunotech). Within the lineage-negative population (A). $CD4^+$ $CD11c^-$ IPCs and $CD11c^+$ blood immature dendritic cells (DCs) were isolated (B). IPCs were plasmacytoids by Giemsa staining (C) and contain rough endoplasmic reticulum and Golgi apparatus under transmission electron microscopy (D). The CD11c+ blood immature DCs display dendrites (E and F).

FIG. 2 Immunoperoxidase staining for IFN-α. (A) Purified CD4+ CD11c−lin−IPCS were stimulated with HSV for 6 hours. (B) The isotope controls for the primary antibody in both cell preparations show no staining.

Figure 3:
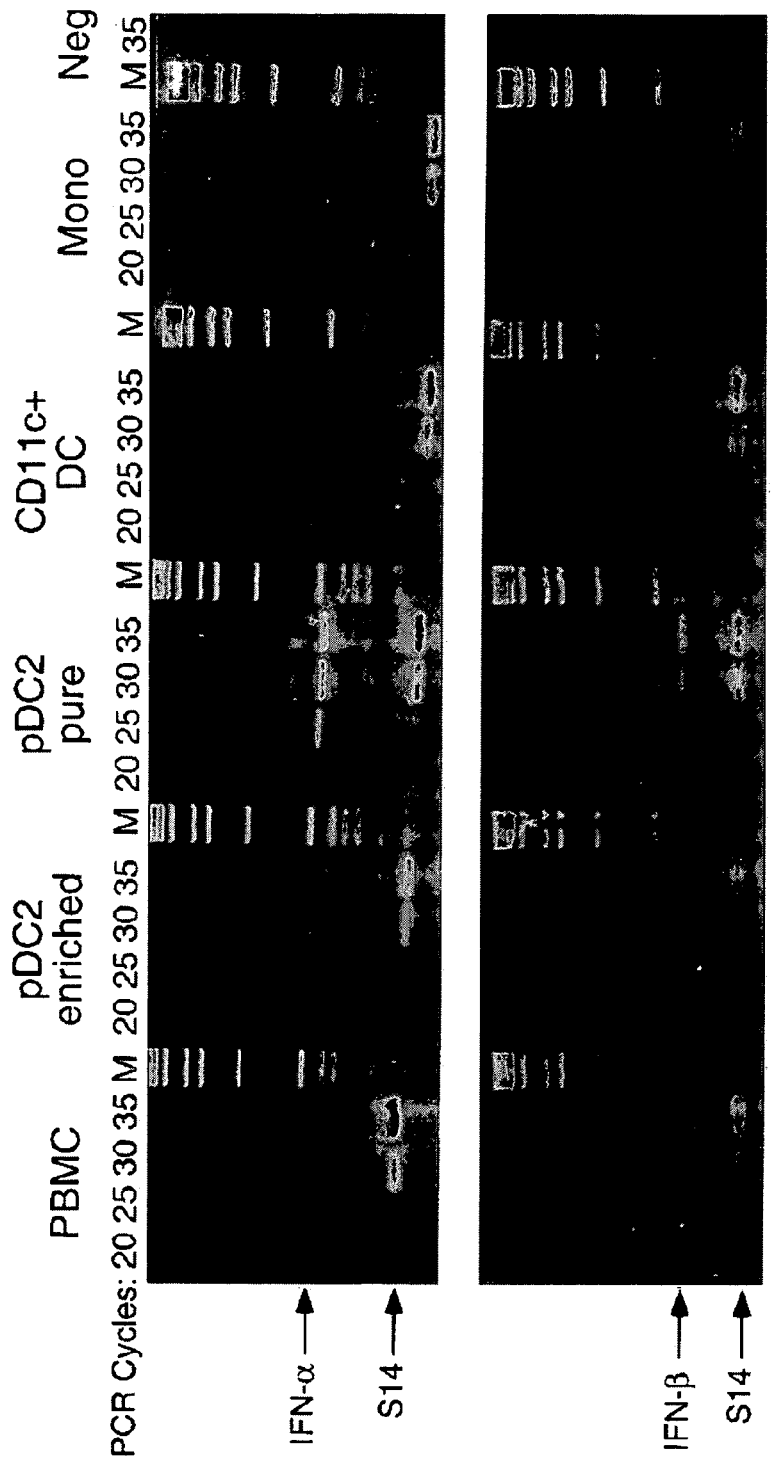

FIG. 3 RT-PCR amplification of IFN-α and IFN-β PCR products amplified from each cell population after 20, 25, 30 or 35 cycles were separated in a 2% agarose gel containing ethidium bromide. Negative controls contained no cDNA Marker is 1-kb DNA Ladder (Life Technologies, Grand Island, N.Y.). IFN-α mRNA is apparent in PBMCs, is increased in the DC2 precursors (pDC2s) with enrichment and purification, and is diminished in the monocytes fraction. IFN-β mRNA is visualized only in the most highly purified DC2 precursors.

Figure 4:
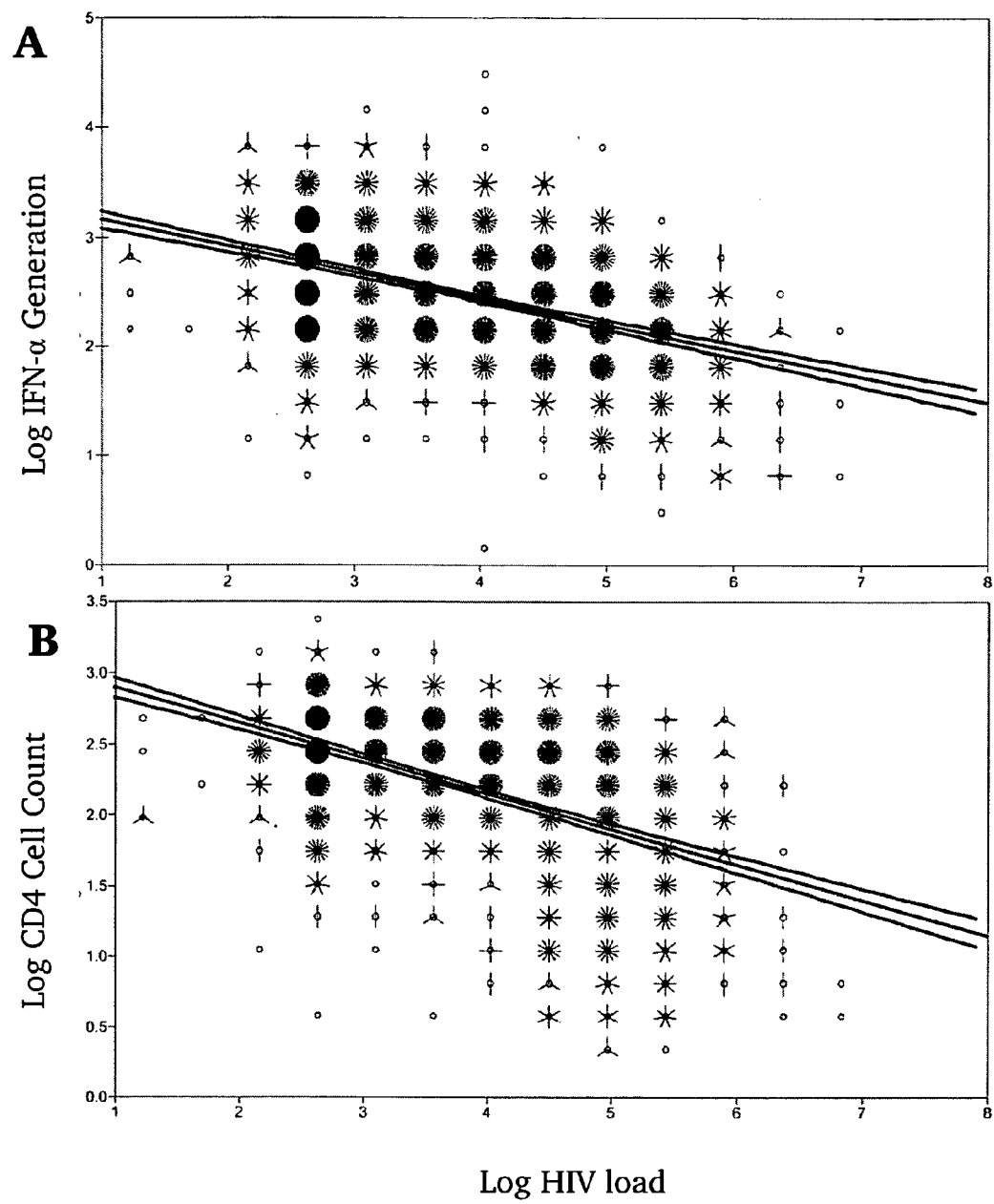

FIG. 4 Relationship of HIV Load to (A) IFN-α Generation and (B) CD4 Count: These scatter diagrams represent all the available data points studied for all subjects with HIV infection. X-axis: log virus load; y-axis: A) log IFN generation and B) log CD4+ cell count. Individual "petals" on these "sunflower" plots show the number of overlapping determinations. Both assays show considerable scatter. The correlation coefficient for log CD4+ cell count (R)=0.498, and for log IFN generation, R=0.428. The regression line slopes (and their ±95% confidence intervals) are shown; the slopes do not differ significantly (see text and Table 1).

Figure 5:
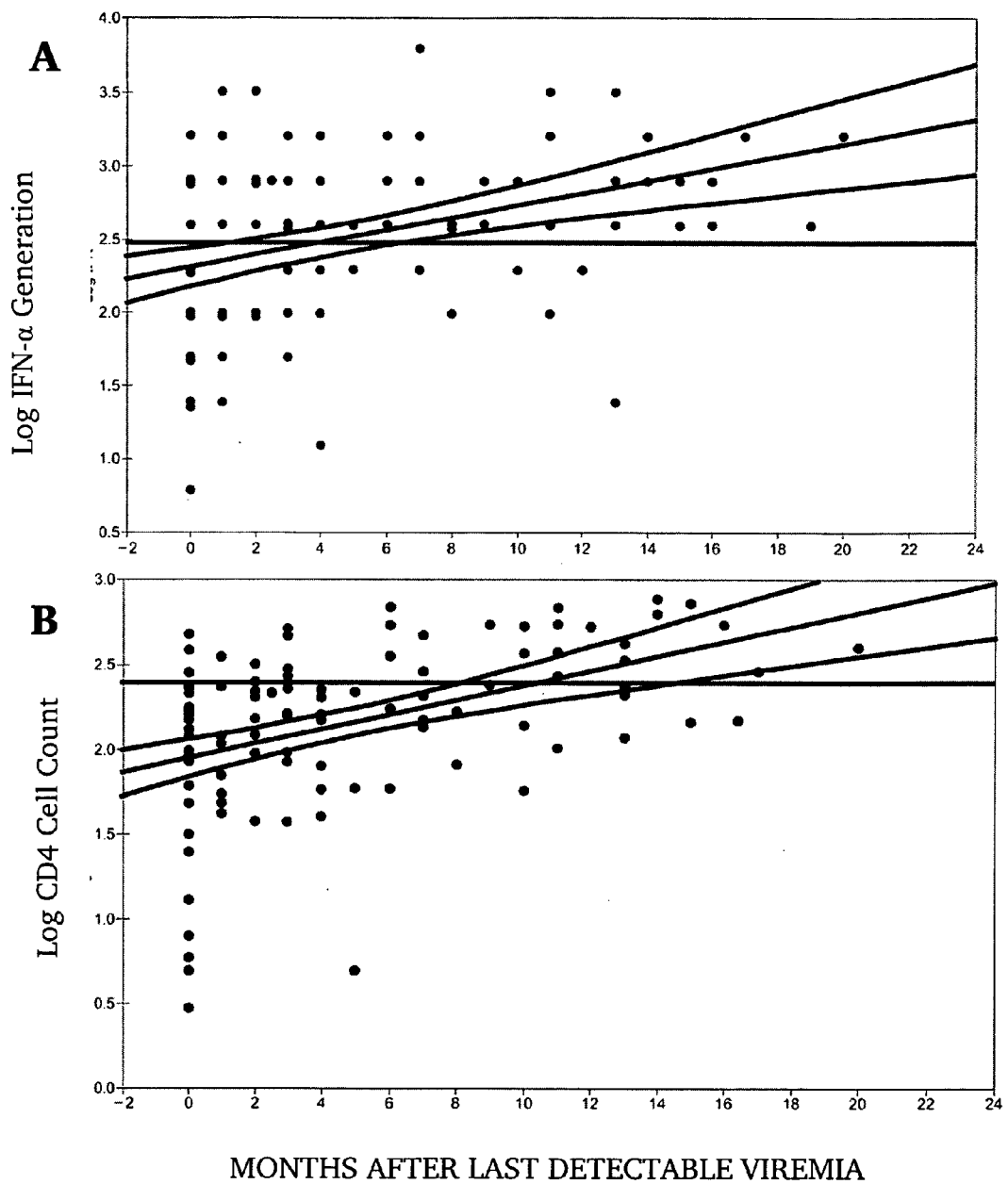
Figure 6A:
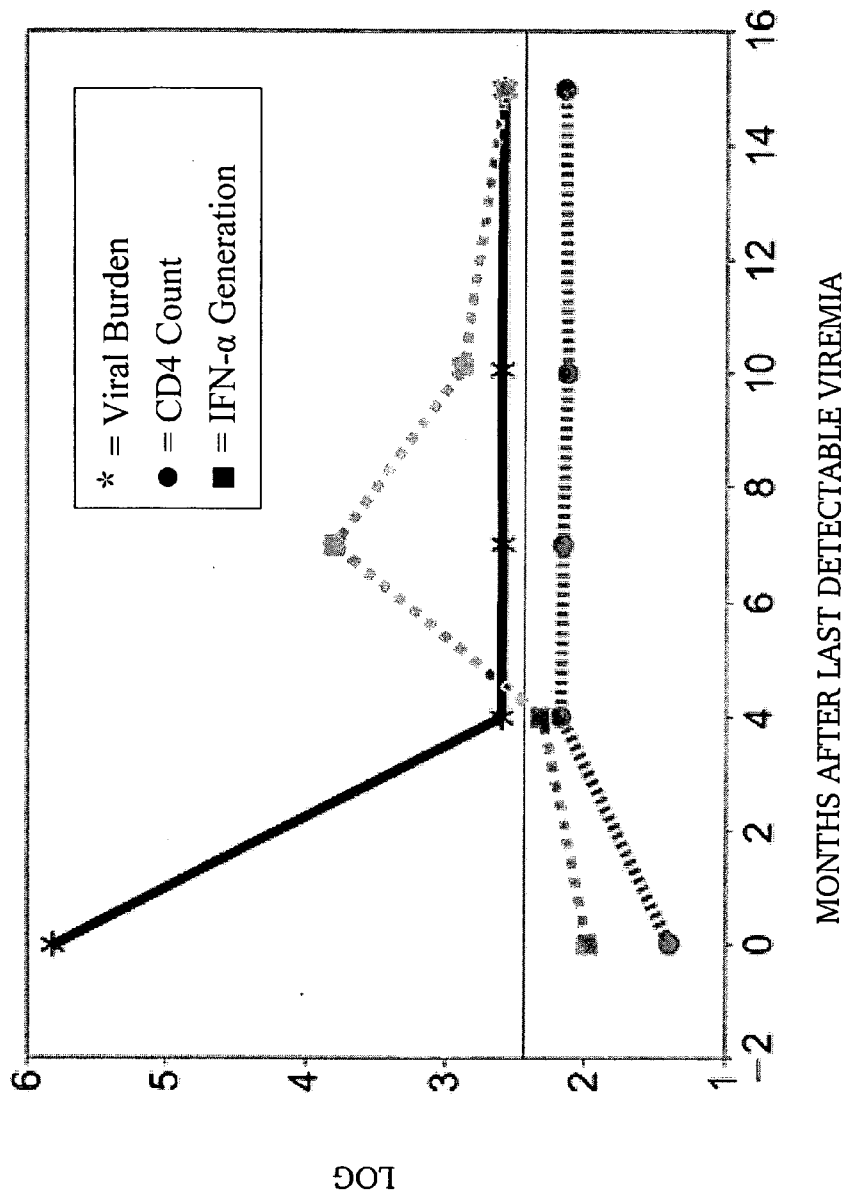
Figure 6B:
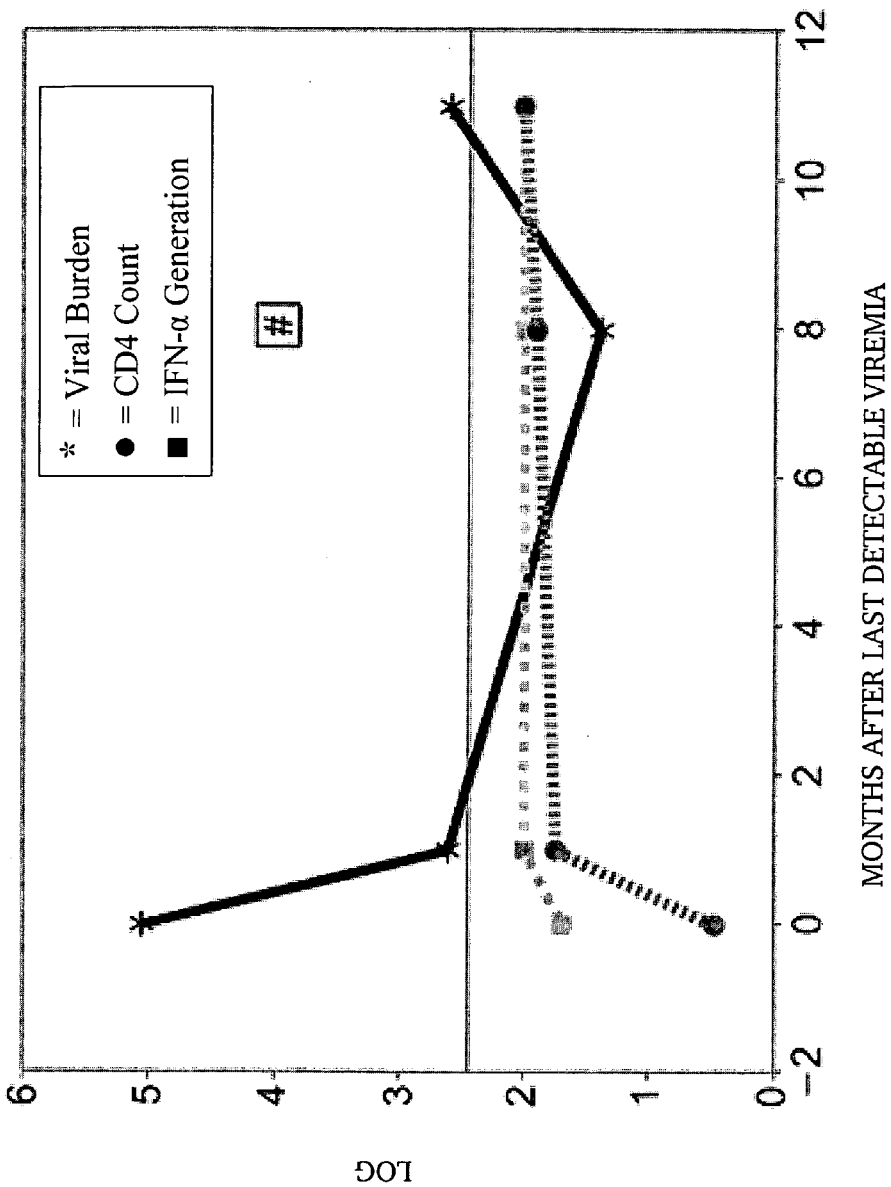

FIG. 5 Time Course of Recovery of (A) IFN-α Generation and (B) CD4 Counts During Therapeutic Viral Suppression: Scatter plots represent all the available data points for 31 subjects with AIDS/OI and virus loads suppressed to <400 copies/mL. Most patients contributed more than two time points to these plots (e.g., FIG. 6), while the virus load remained undetectable (See text and Table 2 for other conditions). The horizontal axis represents months after last detectable viremia; time zero is the last date at which virus loads ≧400 copies/mL were detected. The vertical axis represents log CD4+ count/cu mm or log IU/mL IFN present in supernatants. The horizontal reference lines represent the critically OI-protective levels defined in Siegal et al., 1986, J. Clin. Invest. 78:115–123, CD4=250/cu mm, IFN=300 IU/ml. The regression line for IFN-α generation (shown ± its 95% confidence interval) crosses the critical reference line at around 4 months, while that for CD4 counts crosses at around 10.3 months (see text and Table 2). Reconstitution of IFN-α generation precedes that for CD4+ T cell counts by about 6.3 months.

FIG. 6 Different Patterns of Response to Full Viral Suppression During Antiretroviral Therapy: Axes as in FIG. 2, Y axis reference line at 2.437. (A): Immune recovery after presentation with tuberculosis; reconstitution of CD4+ T cells lags behind IFN-α generation. No new OI developed. (B): Failure of immune recovery despite HIV suppression (Table 3), after presentation with disseminated *Mycobacterium avium* complex (MAC); "#" indicates recurrent MAC bacteremia despite MAC-suppressive therapy.

5. DETAILED DESCRIPTION OF THE INVENTION

The present invention is based, in part, on Applicants' discovery that CD4+ CD3− CD11c− precursor type 2 dendritic cells (pDC2s) are natural type I interferon-producing cells (IPCs). As described in the Example 6 below, pDC2s produce 200 to 1000 times more IFN than blood cells after microbial challenge. Thus, IPCs are an effector cell type of the immune system critical for antiviral and anti-tumor immune responses.

The present invention encompasses compositions for the treatment, inhibition or prevention of diseases or disorders, including cancer, immune diseases or disorders, and infectious diseases affecting or involving IPCs, comprising IPCs and methods of administering the IPCs. The term "interferon-producing cells" or "IPCs" as used herein refers to CD4+ CD3− CD11c− precursor type 2 dendritic cells (pDC2s) isolated or purified from a mammal, preferably a human. In particular, the present invention encompasses therapeutic compositions suitable for administration to animals, preferably mammals and most preferably humans, comprising administering an effective amount of IPCs. IPCs can be locally or systemically administered to an animal, preferably a mammal, and most preferably a human. In one embodiment, purified IPCs are injected, transplanted or implanted in an animal, preferably in a mammal, and most preferably in humans. Cells or tissues of the present invention may be primary or secondary cells or immortalized cell lines. In a preferred embodiment, immortalized IPCs are injected, transplanted or implanted in an animal, preferably in a mammal, and most preferably in a human. Cells or tissues injected, transplanted or implanted in vivo may be autologous or non-autologous. In one embodiment of the present invention, the cells of the present invention are obtained from the individual who is to receive the injection, transplant or implant. This approach might be especially advantageous where immunological rejection of the injection, transplant or implant by the host is likely.

The present invention encompasses compositions for the treatment, inhibition or prevention of diseases or disorders, including cancer, immune diseases or disorders, and infectious disease, comprising purified interferon (IFN) from IPCs and methods of administering the IFN. In particular, the present invention encompasses the therapeutic compositions suitable for administration to animals, preferably mammals and most preferably humans, comprising administering an effective amount of purified IFN from IPCs. IFN can be purified from the supernatant of IPCs cultured in vitro in the presence of IL-3 and an antigen, virus (e.g., HIV, hepatitis B virus or hepatitis C virus) or bacteria (e.g., *Staphylococcus aureus*) using standard techniques known to those of skill in the art. In one embodiment, IFN is purified from the supernatant of IPCs by standard methods including chromatography (e.g., ion exchange, affinity, and sizing column chromatography), centrifugation, differential solubility, or by any other standard technique for the purification of proteins. IFN or a biologically active portion thereof is "isolated" or "purified" when it is substantially free of cellular material or other contaminating proteins from the cell or tissue source from which the protein is derived. The language "substantially free of cellular material" includes preparations of IFN in which the IFN is separated from cellular components of the cells from which it is isolated. Thus, IFN or a biologically active portion thereof that is substantially free of cellular material includes preparations of IFN having less than about 30%, 20%, 10%, or 5% (by dry weight) of heterologous protein (also referred to herein as a "contaminating protein").

The present invention also encompasses therapeutic compositions suitable for administration to animals, preferably mammals and most preferably humans, comprising administering an effective amount of IPCs in combination with at least one other therapeutic agent. The present invention further encompasses therapeutic compositions suitable for administration to animals, preferably mammals and most preferably humans, comprising administering an effective amount of purified IFN from IPCs in combination with at least one other therapeutic agent.

The therapeutic compositions of the present invention are in suitable formulation to be administered to animals, preferably mammals such as companion animals (e.g., dogs, cats, and horses) and livestock (e.g., cows and pigs), and most preferably humans. In a preferred embodiment, the therapeutic compositions of the present invention are in suitable formulation to be administered to humans. The therapeutic compositions of the invention are administered to an animal in an amount effective for the treatment, prevention or inhibition of a disease or disorder (i.e., cancer and infectious diseases), or an amount effective for inducing an anti-tumor response (e.g., the inhibition of the hyperproliferation of a tumor), or an amount effective for the amelioration of one or more symptoms of a disease or disorder, or an amount effective for augmenting the immune response.

The present invention also provides methods for monitoring the progression of a disease or a disorder such as HIV infection or cancer, comprising measuring the abundance of IPCs in lymphoid tissue samples or blood samples from a subject suffering from a disease or disorder. In accordance with the invention, the abundance of purified IPCs or IPC-enriched leukocytes can be measured by trypan blue cell counts, fluorescence-activated cell sorting, or by any other technique known to one of ordinary skill in the art. In a specific embodiment, the abundance of IPCs in the lymphoid tissue samples or blood samples of a human with cancer, an immune disease or disorder, or an infectious disease is measured to monitor disease progression. In a preferred embodiment, the abundance of IPCs in the lymphoid tissue samples or blood samples of a human with HIV is measured to monitor HIV infection or AIDS progression.

In one embodiment, an increase in the number of IPCs in a sample (i.e., lymphoid tissue sample or blood sample) from a subject with HIV infection or AIDS relative to a control sample (from a subject or subjects free of HIV infection or AIDS) or a previously determined reference range indicates that the HIV infection or AIDS is not progressing or not progressing very rapidly. In another embodiment, a decrease in the number of IPCs in a sample (i.e., lymphoid tissue sample or blood sample) from a subject with HIV infection or AIDS relative to a control sample (from a subject or subjects free of HIV infection or AIDS) or a previously determined reference range indicates that the HIV infection or AIDS is progressing.

The present invention also provides methods for determining the effectiveness of a therapeutic or pharmaceutical composition in a subject suffering from a disease or a disorder such as HIV infection or cancer, comprising measuring the abundance of IPCs in lymphoid tissue samples or blood samples from the subject before and after treatment with the therapeutic or pharmaceutical composition. The present invention further provides methods for screening for agents that modulate IPC proliferation or differentiation, or IPC IFN production, secretion or activity.

5.1 Purification of Type I Interferon-Producing Cells

Immune cells can be collected or isolated from blood, or secondary lymphoid organs of the subject, such as but not limited to lymph nodes, tonsils, spleen, Peyer's patch of the intestine, and bone marrow, by any of the methods known in the art. Immune cells obtained from such sources typically comprise predominantly recirculating lymphocytes and macrophages at various stages of differentiation and maturation. Optionally, standard techniques, such as morphological observation and immunochemical staining, can be used, if desired, to verify the presence of the desired cells, e.g., dendritic, T cells, and macrophages. In a preferred aspect, the immune cells used in the in vitro methods of the invention are human peripheral blood compositions lacking red blood cells, e.g., whole blood leukocytes (whole peripheral blood from which the red blood cells and serum have been substantially removed), which can be collected from a human subject by standard techniques, such as by use of a syringe to withdraw the blood, followed by subjecting the blood to Ficoll-Hypaque (Pharmacia) gradient centrifugation. Blood, anticoagulated with preservative-free heparin, usually yields 0.5 to $1 \times 10^6$ lymphocytes/ml. Separated blood cells (e.g., leukocytes) may be frozen by standard techniques prior to use in the present methods. In a specific embodiment, the immune cells used are purified white blood cells comprising lymphocytes and macrophages. An "isolated" or "purified" IPC is substantially free of cellular material or contaminating cells (e.g., T cell, B cells, and NK cells) from the tissue from which the IPCs are derived. The language "substantially free of cellular material or contaminating cells" includes preparations of IPCs having less than about 30%, 20%, 10%, or 5% contaminating cells.

In one embodiment, antibodies against specific surface markers can be directly labeled by conjugation of an affinity compound to such antibodies to facilitate detection and separation of IPCs. Alternatively, in another embodiment, the primary antibody is detected by detecting binding of a secondary antibody or reagent to the primary antibody. In a further embodiment, the secondary antibody is labeled.

Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods (e.g., FACS), affinity chromatography, and panning.

In one embodiment, affinity compounds or affinity tags can be conjugated to the primary or secondary antibodies through a polyfunctional crosslinker, and preferably a bifunctional molecule.

In another embodiment, a labeled ligand specific to IPC surface marker may be used. A ligand may be affinity labeled by the methods used for directly labeling antibody described above. Additionally, a ligand may be labeled using a peptide tag (i.e., a fusion protein) may be used to facilitate identification and/or isolation of the macrophage or antigenic cell. In various embodiments, such a fusion protein can be made by ligating a ligand gene sequence to the sequence encoding the peptide tag in the proper reading frame. A variety of peptide tags known in the art may be used, such as but not limited to the immunoglobulin constant regions, polyhistidine sequence affinity chromatography (in Ausubel et al., eds., 1992, Current Protocols in Molecular Biology, Greene Publishing Associates and Wiley Interscience, New York), glutathione S-transferase (GST; Smith, 1993, Methods Mol. Cell Bio. 4:220–229), the *E. coli* maltose binding protein (Guan et al., 1987, Gene 67:21–30), and various cellulose binding domains (U.S. Pat. Nos. 5,496,934; 5,202,247; 5,137,819; Tomme et al., 1994, Protein Eng. 7:117–123), etc. Other peptide tags may impart fluorescent properties to a ligand or antibody, e.g., portions of green fluorescent protein and the like. Other possible peptide tags are short amino acid sequences to which monoclonal antibodies are available, such as but not limited to the following well known examples, the FLAG epitope, the myc epitope at amino acids 408–439, the influenza virus hemagglutinin (HA) epitope. Other peptide tags are recognized by specific binding partners and thus facilitate isolation by affinity binding to the binding partner which can be immobilized onto a solid support.

In one embodiment, the IPCs may be sorted using a fluorescence-activated cell sorter (FACS). Fluorescence-activated cell sorting (FACS) is a well-known method for separating particles, including cells, based on the fluorescent properties of the particles (Kamarch, 1987, Methods Enzymol, 151:150–165). Laser excitation of fluorescent moieties in the individual particles results in a small electrical charge allowing electromagnetic separation of positive and negative particles from a mixture. In another embodiment, antigenic cell-specific antibody or ligand and antigen-presenting cell-specific antibody or ligand are labeled with distinct fluorescent labels. A first antibody, used to detect an immune cell antigenic determinant present on the cell surface of IPCs is labeled with a fluorochrome, such as FITC or phycoerythrin. A second antibody, labeled with a distinct fluorochrome, recognizes an antigenic determinant present on the IPC. IPCs are incubated with the fluorescently labeled antibodies or ligands for a time period sufficient to allow the labeled antibodies or ligands to bind to cells, preferably between 10 and 60 minutes. Cells are eluted from the beads, and the procedure is repeated a second time. This time, cells are processed through the cell sorter, allowing separation of cells that bind both antibodies to be separated from hybrid cells that do not bind both antibodies. FACS sorted particles may be directly deposited into individual wells of 96-well or 384-well plates to facilitate separation and cloning.

In another embodiment, magnetic beads can be used to separate IPCs. IPCs may be sorted using a magnetic activated cell sorting (MACS) technique, a method for separating particles based on their ability to bind magnetic beads (0.5–100 µm diameter) (Dynal, 1995). A variety of useful modifications can be performed on the magnetic microspheres, including covalent addition of antibody which specifically recognizes a cell-solid phase surface molecule or hapten. A magnetic field is then applied to physically manipulate the selected beads. The beads are then mixed with the immune cells to allow binding. Cells are then passed through a magnetic field to separate out cells expressing IPC surface markers.

5.2. Immortalization of Type I Interferon-Producing Cells

In one embodiment, IPCs which normally undergo spontaneous apoptosis can be immortalized to allow for sustained IFN production. In accordance with this embodiment, normal IPCs (which can be derived from the patient or subject) can be immortalized by genetically engineering the telomerase gene, an oncogene (e.g., mos or v-src), or an apoptosis-inhibiting gene (e.g., bcl-2) into the cells. See, e.g., Katakura et al., 1998, Methods Cell. Biol. 57:69–91 for a review of methods for immortalizing cells by gene engineering. Alternatively, normal IPCs can be immortalized by fusion with a partner cell such as a tumor cell utilizing techniques known to one of skill in the art.

5.3. Genetically Engineering IPCs

In accordance with the present invention, IPCs may be engineered to express any gene product known in the art. For example, IPCs may be engineered to express one or more cytokines (e.g, TNF-α, IL-1, IL-2, IL-3, IL-5, IL-10, IL-12, IL-15, IL-18, granulocyte colony-stimulating factor (G-CSF), GM-CSF and chemokines), one or more oncogenes (e.g., mos or v-src), one or more apoptosis-inhibiting gene products (e.g., bcl-2), or any combination thereof. In one embodiment, IPCs are engineered to express IL-3. In another embodiment, IPCs are engineered to express one or more oncogenes, one or more apoptosis-inhibiting gene products, or a combination thereof. In a preferred embodiment, IPCs are engineered to express IL-3 and at least one oncogene or apoptosis-inhibiting gene product. The polynucleotide sequence encoding cytokines, oncogenes and apoptosis-inhibiting gene products can be obtained from any information available to those of skill in the art (i.e., from Genbank, the literature, or by routine cloning). For example, the polynucleotide sequence of the human IL-3 cDNA is provided in Genbank Accession No. M14743 and Genbank Accession No. M20137, and the polynucleotide sequence of the human bcl-2 mRNA is provided in Genbank Accession No. M14745. Polynucleotide sequences encoding gene products or functionally active fragments thereof can be generated by any method known to those of skill in the art. For example, polynucleotide sequences can be generated by recombinant DNA technology or may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

The nucleotide sequence encoding a cytokine (i.e., TNF-α, IL-1, IL-2, IL-3, IL-5, IL-10, IL-12, IL-15, IL-18, granulocyte colony-stimulating factor (G-CSF), GM-CSF and chemokines), an oncogene (e.g., mos or v-src), an apoptosis-inhibiting gene product, or a functionally active analog or fragment thereof can be inserted into an appropriate expression vector, i.e., a vector which contains the necessary elements for the transcription and translation of the inserted protein-coding sequence. The necessary transcriptional and translational signals can also be supplied by the native gene or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a specific embodiment, the human IL-3 gene is expressed, or sequences encoding functionally active portions of the human IL-3 are expressed in IPCs. In another embodiment, an oncogene is expressed, or sequences encoding functionally active portions of an oncogene are expressed in IPCs. In another embodiment, an apoptosis-inhibiting gene product is expressed, or sequences encoding an apoptosis-inhibiting gene product are expressed in IPCs. In another embodiment, an oncogene and apoptosis-inhibiting gene product are expressed, or sequences encoding an oncogene or apoptosis-inhibiting gene product are expressed in IPCs. In a preferred embodiment, the human IL-3 gene and an oncogene or apoptosis-inhibiting gene product are expressed, or sequences encoding the human IL-3 gene and an oncogene or apoptosis-inhibiting gene product are expressed in IPCs.

Any methods known to one of ordinary skill in the art for the insertion of DNA fragments into a vector may be used to construct expression vectors containing a chimeric gene consisting of appropriate transcriptional and translational control signals and the protein coding sequences. These methods may include in vitro recombinant DNA and synthetic techniques and in vivo recombinants (genetic recombination). See, for example, the techniques described in Sambrook et al., 1989, supra, and Ausubel et al., 1989, supra. Expression of the nucleic acid sequence encoding a gene product such as a cytokine, an oncogene, or an apoptosis-inhibiting gene product, or a functionally active fragment thereof, may be regulated by a second nucleic acid sequence so that the gene product or fragment thereof is expressed in a host transformed with the recombinant DNA molecule. The gene products or functionally active fragments thereof may be engineered to be expressed constitutively or in a tissue-specific or stimuli-specific manner. In accordance with this aspect of the invention, the nucleotide sequences encoding gene products may be operably linked to promoter elements known in the art which are constitutively active, tissue-specific or induced upon presence of a specific stimuli.

Promoters which may be used to control expression of a gene product or fragment thereof include, but are not limited to, the SV40 early promoter region (Bernoist and Chambon, 1981, *Nature* 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. USA 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. USA 75:3727–3731), or the tac promoter (DeBoer et al., 1983, Proc. Natl. Acad. Sci. USA 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315: 338–340; Kollias et al., 1986, *Cell* 46:89–94; myelin basic protein gene control region which is active in oligodendrocytes in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a nucleic acid sequence encoding a gene product or functionally active fragment thereof, one or more origins of replication, and, optionally, one or more selectable markers (e.g., an antibiotic resistance gene).

Expression vectors containing gene inserts can be identified by three general approaches: (a) nucleic acid hybridization, (b) presence or absence of "marker" gene functions, and (c) expression of inserted sequences. In the first approach, the presence of the nucleic acid sequence inserted in an expression vector(s) can be detected by nucleic acid hybridization using probes comprising sequences that are homologous to the inserted gene(s). In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of the gene(s) in the vector(s). For example, if the nucleotide sequence encoding human IL-3 is inserted within the marker gene sequence of the vector, recombinants containing the IL-3 gene insert can be identified by the absence of the marker gene function. In the third approach, recombinant expression vectors can be identified by assaying the gene product expressed by the recombinant. Such assays can be based, for example, on the physical or functional properties of the gene products or functionally active fragments thereof in in vitro assay systems, e.g., binding of IL-3 with anti-IL-3 antibody or binding of bcl-2 with anti-bcl-2 antibody.

Vectors containing nucleotide sequences encoding gene products or functionally active fragments thereof may be transiently or stably transfected into IPCs by any suitable technique, including microinjection, electroporation, lipofection, biolistics, calcium phosphate precipitation, and viral-based vectors, among others. Other methods used to transfect mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y.).

For long-term, high-yield production of recombinant proteins, stable expression is preferred. For example, IPCs which stably express a gene product or functionally active fragment thereof may be engineered. Rather than using expression vectors which contain viral origins of replication, IPCs can be transformed with DNA controlled by appropriate expression control elements (e.g., promoter, enhancer, sequences, transcription terminators, polyadenylation sites, etc.), and a selectable marker. Following the introduction of the foreign DNA, engineered IPCs may be allowed to grow for 1–2 days in an enriched media, and then are switched to a selective media. The selectable marker in the recombinant plasmid confers resistance to the selection and allows cells to stably integrate the plasmid into their chromosomes and grow.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes.

In a specific embodiment of the present invention, IPCs are engineered to express an endogenous gene such as IL-3 and bcl-2 under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. Identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

5.4. Gene Therapy

In one embodiment, nucleic acid molecules comprising sequences encoding one or more gene products (e.g., cytokines, oncogenes and apoptosis-inhibiting gene products) are administered to promote the immune response by way of gene therapy. Gene therapy refers to therapy performed by the administration to a subject of an expressed or expressible nucleic acid. Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

Any of the methods for gene therapy available in the art can be used according to the present invention. For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J. Biol. Chem.* 262:4429–4432) (which can be used to target cell types specifically expressing the receptors), etc. Nucleic acid-ligand complexes can be formed in which the ligand comprises a fusogenic viral peptide to disrupt endosomes, allowing the nucleic acid to avoid lysosomal degradation. In a preferred embodiment, the nucleic acid is targeted in vivo for IPC specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). In another preferred embodiment, the nucleic acid is introduced intracellularly and incorporated within IPC DNA for expression, by homologous recombination (Koller and Smithies, 1989, *Proc. Natl. Acad. Sci. USA* 86:8932–8935; Zijlstra et al., 1989, *Nature* 342:435–438).

In one embodiment, viral vectors, which facilitate delivery of the gene into a patient, that contain nucleic acids encoding gene products (i.e., cytokines, oncogenes and apoptosis-inhibiting gene products) or functionally active fragments thereof are used in gene therapy to target IPCs. Examples of viral vectors which may be used in gene therapy include, but are not limited to, retroviral vectors (see, e.g., Boesen et al., 1994, Biotherapy 6:291–302, Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114), adenoviruses (see, e.g., Kozarsky and Wilson, 1993, Current Opinion in Genetics and Development 3:499–503; Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang, et al., 1995, Gene Therapy 2:775–783), and adeno-associated virus (Walsh et al., 1993, Proc. Soc. Exp. Biol. Med. 204:289–300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and express the transferred gene. Those cells are then delivered to a patient.

In embodiment, the nucleic acid is introduced into IPCs prior to administration in vivo of the resulting recombinant IPCs. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient IPCs are not disrupted. The technique should provide for the stable transfer of the nucleic acid to IPCs, so that the nucleic acid is expressible by IPCs and preferably heritable and expressible by its progeny.

The resulting recombinant IPCs can be delivered to a patient by various methods known in the art. Preferably, the recombinant IPCs are administered intravenously. The amount of IPCs envisioned for use depends on the desired effect, patient state, etc., and can be determined by one skilled in the art.

In a preferred embodiment, the cell used for gene therapy is autologous to the patient.

In one embodiment in which recombinant IPCs are used in gene therapy, nucleic acid sequences encoding one or more cytokines, one or more oncogenes, one or more apoptosis-inhibiting gene products, or a combination thereof are introduced into the cells such that they are expressible by the IPCs or their progeny, and the recombinant IPCs are then administered in vivo for therapeutic effect.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.5. Demonstration of the Utility of the Genetically Engineered Cells

The IPCs of the invention are preferably tested in vitro, and then in vivo for the desired therapeutic or prophylactic activity, prior to use in humans. Expression of a gene(s), such as IFN or bcl-2, can be readily detected, e.g., by quantifying protein and/or RNA. Many methods standard in the art can be thus employed, including but not limited to kinase assays, immunoassays to detect and/or visualize gene expression (e.g., Western blot, immunoprecipitation followed by sodium dodecyl sulfate polyacrylamide gel electrophoresis, immunocytochemistry, etc.) and/or hybridization assays to detect gene expression by detecting and/or visualizing respectively mRNA encoding a gene (e.g., Northern assays, dot blots, in situ hybridization, etc), etc. The activity of a gene product, such as IFN, can be tested by assessing the effect of the tissue culture supernatant from the cells or tissues on different cells in culture. Known effects of a gene (e.g., IFN), such as the activation of a signaling molecule or the induction of a gene product, can be assessed by standard methods known to those of skill in the art. For example, Jak 1 tyrosine phosphorylation induced in response to IFN can be measured by immunoprecipitation followed by Western blot analysis. Stat1 activity induced by IFN can be measured, for example, by electromobility shift assay ("EMSA") and by detecting the expression of a gene whose expression is controlled by a promoter that is responsive to Stat1.

IPCs for use in vivo can be tested in suitable animal model systems prior to testing in humans, including but not limited to rats, mice, chicken, cows, monkeys, rabbits, etc. For in vivo testing, prior to administration to humans, any animal model system known in the art may be used.

5.6. Therapeutic Uses of Compositions

The invention provides for treatment, prevention or inhibition of diseases and disorders, including cancer, immune diseases and infectious diseases by administration of a therapeutic composition. In a preferred embodiment, therapeuic compositions are administered to a subject to treat, prevent or inhibit cancer. Examples of types of cancer, include, but are not limited to, neoplasms, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease, metastases, or any disease or disorder characterized by uncontrolled cell growth.

In another embodiment, therapeutic compositions are administered to a subject to treat, prevent or inhibit immune diseases. Examples of immune diseases include, but are not limited to, autoimmune disorders (e.g., arthritis, graft rejection such as allograft rejection, autoimmune thyroiditis, Type I diabetes mellitus, insulin-resistant diabetes, autoimmune anemia, multiple sclerosis, lupus, sclerodoma, allergic rhinitis and food allergies, asthma, psoriasis, and transplantation rejection), and inflammatory disorders (e.g., bacterial infection, psoriasis, septicemia, cerebral malaria, inflammatory bowel disease, arthritis). In another embodiment, therapeutic compositions are administered to a subject to treat, prevent or inhibit infectious diseases. Infectious diseases include diseases associated with yeast, fungal, viral and bacterial infections. Viruses causing viral infections include, but are limited to, herpes simplex virus (HSV), hepatitis B virus (HBV), hepatitis C virus (HCV), human T-cell lymphotrophic virus (HTLV) type I and II, human immunodeficiency virus (HIV), cytomegalovirus, papilloma virus, polyoma viruses, adenoviruses, Epstein-Barr virus, poxviruses, influenza virus, measles virus, rabies virus, Sendai virus, poliomyelitis virus, coxsackieviruses, rhinoviruses, reoviruses, and rubella virus. Microbial pathogens causing bacterial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

In specific embodiments, a subject is administered a composition of the present invention in an amount effective for the treatment, prevention or inhibition of a disease or disorder such as cancer and an infectious disease, or an amount effective for inducing an anti-tumor response (e.g., the inhibition of the hyperproliferation of a tumor), an amount effective such that the immune response in a subject is augmented. The term "augment" as used herein refers to an increase in the biological activity (e.g., the proliferation, differentiation, priming, effector function, production of cytokines or expression of antigens) of immune cells such as T cells, B cells, natural killer cells, dendritic cells, and macrophages. In particular, IPCs or IFN isolated from IPCs augments the immune response when the biological activity of immune cells is increased 1–5 fold, 5–10 fold, 10–20 fold or more than 20 fold as compared to the biological activity of the immune cells in the absence of IPCs or IFN isolated from IPCs. The biological activity of immune cells can be determined by assays known to those of skilled in the art, in particular those assays described herein which measure the proliferation and the expression of cytokines and antigens.

In one embodiment, an animal is administered one or more therapeutic compositions of the invention in combination with one or more known antiviral agents for the treatment, prevention or inhibition of a viral infection. Examples of antiviral agents include, but are not limited to, acyclovir, AZT, and amantadine. In another embodiment, an animal is administered one or more therapeutic compositions of the invention in combination with one or more known agents for the treatment, prevention or inhibition of immune disorders (e.g., chemotherapeutic agents or anti-tumor antigen antibodies) or infectious diseases (e.g., antibiotics).

5.6. Administration of Compositions of the Invention

The invention provides methods of treatment (and prophylaxis) by administration to a subject of an effective amount of a therapeutic composition of the invention. In a preferred aspect, the therapeutic compositions is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a preferred embodiment, a human is the subject.

Various delivery systems are known and can be used to administer a therapeutic composition of the invention, e.g., encapsulation in liposomes, microparticles, microcapsules, Methods of introduction include but are not limited to intratumoral, intradermal, intramuscular, intraperitoneal, intravenous, subcutaneous, intranasal, epidural, and oral routes. The therapeutic compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the therapeutic compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic composition can be delivered in a vesicle, in particular a liposome (see Langer, *Science* 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In another embodiment, the therapeutic composition can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment of the present invention, IPCs are encapsulated as described for delivery in vivo, e.g., in U.S. Pat. Nos. 5,874,099, 4,744,933, and 4,409,331; each of which is incorporated herein by reference in their entirety. In a preferred embodiment of the present invention, the encapsulation of IPCs of the present invention: (i) protects cells or tissues from destruction by the host's immune system; (ii) enables nutrients and oxygen to diffuse into the capsule to sustain the cells or tissues; (iii) enables the cells or tissues to be readily retrieved; (iv) is biocompatible; (v) does not induce the formation of scar tissue. In one embodiment, the capsule in which the cells and tissues are encased is biodegradable.

The present invention also provides therapeutic compositions comprising a therapeutically effective amount of IPCs or IFN isolated from IPCs, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a specific embodiment, the composition is formulated in accordance with routine procedures adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. In cases where the composition to be administered by infusion comprises IFN isolated from IPC, it can be dispensed with an infusion bottle containing sterile pharmaceutical grade water or saline. Where the composition to be administered by injection comprises IFN isolated from IPCs, an ampoule of sterile water for injection or saline can be provided so that the ingredients may be mixed prior to administration. Where the composition to be administered by infusion or injection comprises IPCs, it can be dispensed in saline solution such as phosphate buffered saline ("PBS").

The amount of the therapeutic composition of the invention which will be effective in the treatment of diseases and disorders can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, a suitable dosage range for intravenous administration of a protein such as IFN is generally about 20–500 micrograms of active protein per kilogram body weight. A suitable dosage range for intranasal administration of a protein such as IFN is generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the therapeutic compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.7. Monitoring the Progression of Diseases or Disorders

In accordance with the present invention, the progression of a disease or a disorder such as an infectious disease, an immune disorder or cancer can be monitored by measuring the abundance of IPCs in a lymphoid tissue sample or blood sample from a subject suffering from a disease or disorder. The abundance (i.e., number) of IPCs in a sample can be measured by trypan blue cell counts, fluorescence-activated cell sorting, or by any other technique known to one of ordinary skill in the art. IPCs can be purified from the lymphoid tissue samples or blood samples or enriched before measuring their abundance. In a specific embodiment, the abundance of IPCs in a lymphoid tissue sample or blood sample of a human with cancer, an immune disorder, or an infectious disease is measured to monitor disease or disorder progression.

In one embodiment, an increase in the number of IPCs in a sample (i.e., lymphoid tissue sample or blood sample) from a subject with a disease or disorder relative to a control sample or a previously determined reference range may indicate, depending upon the disease or disorder, the progression of the disease or disorder. For example, an increase in the number of IPCs in a sample obtained from a subject with an autoimmune disease or leukemia relative to a control sample or a previously determined reference range may indicate the progression of the autoimmune disease or leukemia. In another embodiment, a decrease in the number of IPCs in a sample (i.e., lymphoid tissue sample or blood sample) from a subject with a disease or disorder relative to a control sample or a previously determined reference range may indicate, depending upon the disease or disorder, the progression of the disease or disorder. For example, a decrease in the number of IPCs in a sample obtained from a subject with an infectious disease or a solid tumor relative to a control sample or a previously determined reference range indicates the progression of the infectious disease or tumor.

In a preferred embodiment, the abundance of IPCs in a lymphoid tissue sample or blood sample of a human with HIV is measured to monitor HIV infection or AIDS progression. In another embodiment, an increase in the number of IPCs in a sample (i.e., lymphoid tissue sample or blood sample) from a subject with HIV infection or AIDS relative to a control sample (from a subject or subjects free of HIV infection or AIDS) or a previously determined reference range indicates that the HIV infection or AIDS is not progressing or not progressing very rapidly. In another embodiment, a decrease in the number of IPCs in a sample (i.e., lymphoid tissue sample or blood sample) from a subject with HIV infection or AIDS relative to a control sample (from a subject or subjects free of HIV infection or AIDS) or a previously determined reference range indicates that the HIV infection or AIDS is progressing.

In another aspect of the present invention, the effectiveness of a therapeutic or pharmaceutical composition in treating, inhibiting or ameliorating a symptom in a subject suffering a disease or disorder such as an infectious disease, an immune disorder or cancer is determined by measuring and comparing the abundance of IPCs in lymphoid organs or blood samples from the subject before and after treatment with the therapeutic or pharmaceutical composition. The abundance of purified IPCs or IPC-enriched leukocytes can be measured by trypan blue cell counts, fluorescence-activated cell sorting, or by any other technique known to one of ordinary skill in the art. In a preferred embodiment, the effectiveness of a therapeutic or pharmaceutical composition in treating, inhibiting or ameliorating a symptom is determined by measuring and comparing the abundance of IPCs in a subject with HIV infection or AIDS before and after the administration of the therapeutic or pharmaceutical composition.

In a specific embodiment, an increase in the abundance of IPCs in a sample (i.e., lymphoid tissue sample or blood sample) following the administration of a therapeutic or pharmaceutical composition to a subject relative to a control sample (from a subject or subjects prior to the administration of the therapeutic or pharmaceutical composition) or a previously determined reference range indicates that the therapeutic or pharmaceutical composition was effective in inducing or augmenting an immune response. In another embodiment, an increase in the abundance of IPCs in a sample (i.e., lymphoid tissue sample or blood sample) following the administration of a therapeutic or pharmaceutical composition to a subject relative to a control sample (from a subject or subjects prior to the administration of the therapeutic or pharmaceutical composition) or a previously determined reference range may indicate, depending upon the disease or disorder, that the therapeutic or pharmaceutical composition was effective in treating the disease or disorder. For example, an increase in the number of IPCs in a sample obtained from a subject with an infectious disease or a solid tumor following administration of a therapeutic or pharmaceutical composition relative to a control sample or a previously determined reference range indicates that the therapeutic or pharmaceutical composition is effective in treating the infectious disease or tumor.

In a specific embodiment, a decrease in the abundance of IPCs in a sample (i.e., lymphoid tissue sample or blood sample) following the administration of a therapeutic or pharmaceutical composition to a subject relative to a control sample (from a subject or subjects prior to the administration of the therapeutic or pharmaceutical composition) or a previously determined reference range indicates that the therapeutic or pharmaceutical composition was effective in inhibiting or reducing an immune response. In another embodiment, a decrease in the abundance of IPCs in a sample (i.e., lymphoid tissue sample or blood sample) following the administration of a therapeutic or pharmaceutical composition to a subject relative to a control sample (from a subject or subjects prior to the administration of the therapeutic or pharmaceutical composition) or a previously determined reference range may indicate, depending upon the disease or disorder, that the therapeutic or pharmaceutical composition was ineffective in treating the disease or disorder. For example, a decrease in the number of IPCs in a sample obtained from a subject with an autoimmune disease or leukemia following the administration of a pharmaceutical or therapeutic composition relative to a control sample or a previously determined reference range indicates that the therapeutic or pharmaceutical composition was ineffective in treating the autoimmune disease or leukemia.

In another embodiment, a decrease in the abundance of IPCs in a sample (i.e., lymphoid tissue sample or blood sample) following the administration of a therapeutic or pharmaceutical composition to a subject relative to a control sample (from a subject or subjects prior to the administration of the therapeutic or pharmaceutical composition) or a previously determined reference range may indicate, depending upon the disease or disorder, that the therapeutic or pharmaceutical composition was effective in treating the disease or disorder. For example, a decrease in the number of IPCs in a sample obtained from a subject with an autoimmune disease or leukemia following the administration of a pharmaceutical or therapeutic composition relative to a control sample or a previously determined reference range indicates that the therapeutic or pharmaceutical composition was effective in treating the autoimmune disease or leukemia. In another example, a decrease in the number of IPCs in a sample obtained from a subject with an inflammatory disorder or an autoimmune disease following administration of corticosteriod drugs relative to a control sample or a previously determined reference range indicates that the therapeutic or pharmaceutical composition was effective in treating the inflammatory or autoimmune disorder.

5.8. Imaging

Labeled antibodies, derivatives and analogs thereof, which specifically bind to cell surface antigens such as CD4 on the surface of IPCs can be used for diagnostic purposes to detect or monitor diseases or disorders such as infectious diseases, immune disorders, and cancer. Molecules capable of specifically recognizing cell surface antigens, including, but not limited to, antibodies, derivatives (including but not limited to fragments) and analogs thereof, and peptides and peptide mimetics can be used to detect IPCs in vivo. Antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Any procedure known to those of skill in the art can be used to generate antibodies specific for surface antigens expressed by IPCs (see, e.g., 6,066,498, which is incorporated herein in its entirety). Preferably, monoclonal antibodies that specifically bind to and recognize IPC surface antigens are used to detect IPCs in vivo. Any procedure known to those of skill in the art for generating peptides and peptide mimetics which specifically bind to and recognize IPC surface antigens are used to detect IPCs in vivo. In a preferred embodiment, diseases or disorders are detected in the patient. The patient is an animal, preferably a mammal and most preferably a human.

In an embodiment, diagnosis is carried out by: a) administering to a subject an effective amount of a labeled molecule which specifically binds to cell surface antigen on IPCs; b) waiting for a time interval following the administering for permitting the labeled molecule to preferentially concentrate at any cancerous site in the subject (and for unbound labeled molecule to be cleared to background level); c) determining background level; and d) detecting the labeled molecule in the subject, such that detection of labeled molecule above the background level indicates the presence of cancer. Background level can be determined by various methods including, comparing the amount of labeled molecule detected to a standard value previously determined for a particular system.

Depending on several variables, including the type of label used and the mode of administration, the time interval following the administering for permitting the labeled molecule to preferentially concentrate on IPCs in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the diseases or disorders is carried out by repeating the method, for example, one month after initial diagnosis, six months after initial diagnosis, one year after initial diagnosis, etc.

5.8.1. Methods of Detection and Imaging

Presence of a labeled molecule can be detected in a patient using methods known in the art for in vivo scanning. These methods depend upon the type of label used. Skilled artisans will be able to determine the appropriate method for detecting a particular label. Methods and devices that may be used in the diagnostic methods of the invention include but are not limited to: computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

5.9. Screening Assays for Compounds That Modulate IPC Proliferation, Differentiation or Interferon Production The invention provides methods for identifying agents (e.g., candidate compounds or test compounds) that modulate the proliferation or differentiation of IPCs. The invention also provides methods of identifying agents, candidate compounds or test compounds that modulate the expression or activity of IFN produced by IPCs. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g., presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222: 301–310), each of which is incorporated herein in its entirety by reference.

In one embodiment, agents that modulate IPC proliferation or differentiation are identified in a cell-based assay system. In accordance with this embodiment, IPCs are contacted with a candidate compound or a control compound and the ability of the candidate compound to modulate the proliferation or differentiation of IPCs is determined. If desired, this assay may be used to screen a plurality (e.g. a library) of candidate compounds. The ability of the candidate compound to modulate IPC proliferation or differentiation can be determined by methods known to those of skill in the art. For example, the proliferation of IPCs can be assessed by flow cytometry (e.g., propidium iodine labeled cells), $^3$H-thymidine incorporation assays and trypan blue cell counts. The ability of the candidate compound to modulate IPC differentiation can be determined by flow cytometry (i.e., staining cell surface markers), immunoprecipitation and Western blot analysis, and cellular morphology. Suitable control compounds include phosphate buffered saline (PBS) and normal saline (NS).

In another embodiment, agents that modulate the expression or activity of IFN produced by IPCs are identified in a cell-based assay system. In accordance with this embodiment, IPCs are contacted with a candidate compound or a control compound and the ability of the candidate compound to modulate the expression or activity of IFN produced by IPCs is determined. If desired, this assay may be used to screen a plurality (e.g. a library) of candidate compounds. The ability of the candidate compound to modulate the expression or activity of IFN produced by IPCs can be determined by methods known to those of skill in the art. For example, mRNA expression can be assessed by Northern blot analysis or RT-PCR, and protein levels can be assessed by western blot analysis. The activity of IFN produced by IPCs can be assessed by detecting induction of a cellular signal transduction pathway of IFN (e.g., Jak1, Tyk2, Stat1, Stat2, p48), detecting catalytic or enzymatic activity of the target on a suitable substrate, detecting the induction of a reporter gene (e.g., a regulatory element that is responsive to IFN and is operably linked to a nucleic acid encoding a detectable marker, e.g., luciferase), or detecting a cellular response, for example, cellular differentiation, or cell proliferation. In particular, Jak 1 tyrosine phosphorylation induced in response to IFN can be measured by immunoprecipitation followed by Western blot analysis. Further, Stat1 activity induced by IFN can be measured, for example, by electromobility shift assay ("EMSA") and by detecting the expression of a gene whose expression is controlled by a promoter that is responsive to Stat1. Suitable control compounds include phosphate buffered saline (PBS) and normal saline (NS).

6. EXAMPLE

Method of Purifying and Identifying Type I Interferon-Producing Cells

This example demonstrates that type 2 dendritic cell precursors (pDC2s) produce 200 to 1000 times more interferon than other blood cells after microbial challenge.

6.1. Materials and Methods

Isolation of Cells

Human peripheral blood cells were separated into the following populations (Grouard et al., 1997, J. Exp. Med. 185: 1101; Rissoan et al., 1999, Science 283: 1183): (i) monocytes (over 90% purity), obtained by centrifugation through 52% Percoll, then magnetic-bead depletion of B, T, and natural killer (NK) cells; (ii) $CD4^+$ $CD3^-$ $CD11c^+$ immature DCs (99%) purity and (iii) $CD4^+$ $CD3^-$ $CD11c^-$ pDC2s (99% purity), obtained by magnetic-bead depletion of B, T, NK cells, and monocytes, followed by fluorescence-activated cell sorting (FACS) (FIG. 1, A and B); (iv) pDC2-depleted blood mononuclear cells; and (v) pDC2-enriched blood mononuclear cells (Grouard et al., 1997, J. Exp. Med. 185: 1101). pDC2s have a plasmacytoid morphology, with rough endoplasmic reticulum and Golgi apparatus (FIG. 1, C and D). The $CD11c^+$ blood immature DCs display short dendrites (FIG. 1, E and F). The frequency of pDC2s in human blood mononuclear cells is less than 0.5% and increased to 3 to 10% after magnetic-bead depletion of lineage-positive cells. The pDC2-depleted population contains B, T, NK cells, monocytes and DCs.

Analysis of Interferon Production

Cells were incubated with UV-irradiated HSV in quadruplicate wells ($2\times10^5$ cells in 200 µl of culture medium per well with $2\times10^4$ plaque-forming units of virus in 96-well culture plates) (Siegal et al., 1994, Leukemia 8: 1474). IFN in supernatants from 24 hour cultures with and without IL-3 were analyzed with cytopathic reduction in human foreskin fibroblast monolayers cultured with vesicular stomatitis virus (sensitivity, 2 to 25 IU of IFN/ml) (Siegal et al., 1994, Leukemia 8: 1474). Cytocentrifuge preparations of cells from 6 hour cultures were prepared for IFN-α immunostaining with mouse monoclonal antibody 7N4-1 (10 µg/ml; Schering-Plough Research Institute, Kenilworth, N.J.).

IFN-α and IFN-β mRNA expression was analyzed by reverse transcriptase polymerase chain reaction (RT-PCR). Briefly, RNA was isolated with the acid guanidinium thiocyanate-phenol-chloroform method. DNA contamination was removed by digestion with deoxyribonuclease I (5 U; Boehringer-Mannheim, Indianapolis, Ind.) for 30 minutes at 37° C. Controls without reverse transcriptase (RT) were performed. Reverse transcription was carried out with pd(T) 12–18 (Pharmacia, Alameda, Calif.) priming and Superscript II RT (Life Technologies, Grand Island, N.Y.). The PCR reaction volume was 25 µl and contained 100 ng of each primer, 40 nM of each deoxynucleoside triphoshpate, 1 µl of cDNA and 1.25 U of AmpliTaq (Perkin-Elmer, Foster City, Calif.). The primers used were as follows:

IFN-α sense:     5' - GAT GGC CGT GCT GGT GCT CA - 3'              (SEQ ID NO:1)

antisense: 5' - TGA TTT CTG CTC TGA CAA CCT CCC - 3'         (SEQ ID NO:2)

probe:     5' - CTC AAG CCA TCT CTG TCC TCC ATG AGA TGA - 3' (SEQ ID NO:3)

IFN-β sense:     5' - TTG AAT GGG AGG CTT GAA TA - 3'              (SEQ ID NO:4)

antisense: 5' - CTA TGG TCC AGG CAC AGT GA - 3'              (SEQ ID NO:5)

probe:     5' - GGC TGG AAT GAG ACT ATT GTT GAG AAC CTC - 3' (SEQ ID NO:6)

Ribosomal protein S14 sense:     5' - GGC AGA CCG AGA TGA ATC CTC A - 3'           (SEQ ID NO:7)

antisense: 5' - CAG GTC AGG GGT CTT GGT CC - 3'              (SEQ ID NO:8)

(See Siegal et al., 1999, Science 284: 1837–1841, which is incorporated herein in its entirety.) Each PCR amplification contained primers for ribosomal protein S14 to verify the amounts of cDNA. A GeneAmp PCR system 9700 (Perkin-Elmer/Applied Biosystems) was used with an initial denaturation step of 94° C. for 5 minutes, followed by cycles of 94° C. for 30 seconds, 60° C. for 30 seconds, 72° C. for 60 seconds, and a final elongation step of 72° C. for 7 minutes. PCR products were separated on a 2% agarose gel, followed by DNA blotting and hybridization with $^{32}$P-labeled probes.

6.2. Results

IFN production by total peripheral blood mononuclear cells (PBMCs) from three donors was 40, 500, and 700 international units (IU)/$2\times10^5$ cells (Table 1). There was a four to six times increase in IFN production from pDC2-enriched blood mononuclear cells (180 to 2800 IU/$10^5$ cells) and a 180 to 911 times increase in IFN generation from purified pDC2s (20,000 to 638,000 IU/$10^5$ cells). pDC2-depleted PBMCs, immature CD11c$^+$ DCs, monocytes, and monocyte-derived DC1s produced little or low levels of IFN. The ability of pDC2s to produce IFN was decreased after maturation into DC2s by culture with IL-3 or IL-3 plus CD40L for 6 days (Table 1). The geometric mean IFN-α generation by pDC2s was approximately 1 IU/cell, similar to previous estimates (Fitzgerald-Bocarsly, 1993, Pharmacol. Ther. 60:39). Immunoperoxidase staining for human IFN-α confirmed that most PDC2s contained IFN-α protein after 6 hours of exposure to HSV (FIG. 2). Analysis of IFN-α and IFN-β mRNA by polymerase chain reaction (PCR) showed that among human blood cells, pDC2s were making the most IFN-α amd IFN-β mRNA (FIG. 3). Thus, the blood cells responsible for IFN generation in response to HSV, previously known as the IPCs, are actually the DC2 precursors. These cells can be traced and isolated by their expression of CD4 or IL-3 receptor after depletion of cells expressing lineage markers and CD11c (Grouard et al., 1997, J. Exp. Med. 185:1101; Rissoan et al., 1999, Science 283: 1183).

The purified IPCs also produced high levels of IFN in response to Sendai virus and heat-killed *Staphylococcus aureus*, confirming the previous studies in PBMCs and partially purified IPCs (Fitzgerald-Bocarsly, 1993, Pharmacol. Ther. 60:39; Kirchner et al., 1979, Immunobiology 156:65; Peter et al., Eur. J. Immunol. 10:547; Abb et al., Clin Exp. Immunol. 52:179; Perussia et al., 1985, Nat. Immun. Cell Growth Regul. 4:120; Chehlml et al., 1989, Immunology 68:488; Sandberg et al., 1991, Scan. J. Immunol. 34:565; Starr et al., 1993, Acv. Exp. Med. Biol. 329:173; Svensson et al., 1996, Scan. J. Immunol. 44:164; Feldman et al., 1994, Virology 204:1; Feldman et al., 1990, J. Interferon Res. 10:435; Perbas et al., 1995, J. Leukocyte Biol. 57:214; Ghanekar et al., 1996, J. Immunol. 157:4028). The ability of UV-irradiated virus and heat-killed bacteria to induce IFN production by IPCs suggests that viral infection is not required for triggering IFN production. The rapid production of IFN by IPCs represent an effector cell type of the innate immune system. Applicants propose that the IPCs/pDC2s should be included in the hematopoietic developmental chart as a distinct cell lineage. IPCs/pDC2s function as professional IFN-producing cells at the precursor stages and as professional antigen-presenting type 2 Dcs upon terminal differentiation.

Table 1. Precursor DC2 cells are the natural IFN-producing Cells. Cells ($2\times10^5$) were cultured for 24 hours with HSV. Without HSV, IFN activity from different cell types was less than 12.5 U/ml (24). PBMC: total blood mononuclear cells; pDC2-dep: blood mononuclear cells positively selected for expressing CD3, CD11c, CD19, CD14 and CD56; pDC2-enriched: blood mononuclear cells that were depleted of cells expressing CD3, CD19, CD14 and CD56; pDC2: FACS-sorted CD4 CD11c lin cells; CD11c$^+$ DC: FACS-sorted CD11c+lin-immature DCs; Mo: monocytes DC1: monocyte-derived DCs after 6 days if culture with either granulocyte-macrophage colony-stimulating factor (GM-CSF)+IL-4 or GM-CSF+IL-4+CD40 ligand (Siegal et al., 1994, Leukemia 8:1474); DC2: pDC2-derived DCs after 6 days of culture with IL-3+CD40 ligand (Siegal et al., 1994, Leukemia 8:1474). ND, not determined.

| | IFN (U/ml) | | | | | | |
|---|---|---|---|---|---|---|---|
| | PBMC | pDC2-dep | pDC2-enriched | pDC2 | CD11cDC | Mo | DC1 | DC2 |
| Exp. 1 | 500 | ND | 2,800 | 89,800 | 120 | ND | <12.5 | T.100 |
| Exp. 2 | 40 | <12.5 | 180 | 20,000 | <12.5 | 350 | <12.5 | <12.5 |
| Exp. 3 | 700 | 40 | 2,800 | 638,000 | 70 | 90 | ND | ND |

7. EXAMPLE

Cultivating IPC

IPC die rapidly in standard serum-containing medium. IL-3 maintains the cells in culture for longer periods. Cultivating the IPC in the absence of serum or any other protein supplement, except for IL-3 for up to week results in IPC that retain functional activity, as assessed by IFN-alpha production following HSV challenge. Further, cultivating IPC in serum-free media and IL-3 results in a shift to lower density of the IPC, as revealed by Percoll density analyses. Prior to IL-3 incubation, a 48–50–52% discontinuous Percoll density gradient revealed a distribution of IPC activity as follows: 9.5% of activity in top layer; 66% in middle layer; and 24% in the densest fraction. Following a 48 hour incubation in serum-free media supplemented with IL-3, recentrifugation on a discontinuous Percoll density gradient resulted in the following distribution: 83% of activity in top layer; 13% in middle layer; and 4% in the densest fraction. These results indicate that both the maintenance of activity and shift in cell density is due to IL-3 exposure.

8. EXAMPLE

IFN-α Generation and Immune Reconstitution During Anti-Retroviral Therapy for HIV Infection This example demonstrates that IFN-α generation and CD4$^+$ T cells indicate an improvement in the immune response to HIV infection.

8.1. Materials & Methods

Study Population

Between March 1995 and June 1998, 294 unselected consecutive patients at all stages of HIV infection were studied prospectively. There were 59.7% men and 40.3% women; 30.1% were male homosexuals, 29.5% (mostly female) heterosexually infected, 28.8% intravenous drug users, 5.0% third world immigrants, 3.3% hemophiliacs, 1.7% transfusional, and 1.3%, occupational needle-stick recipients. There were 82 (28%) with AIDS and an opportunistic infection (OI); 22 (7%) with AIDS and a non-opportunistic infection (non-OI) case-defining illness (e.g., lymphoma and wasting; (footnote, Table 3)); 79 (26%) with non-AIDS manifestations of HIV infection (e.g., monodermatomal zoster, oral candidiasis, and molluscum contagiosum). Sixty-one percent of the subjects thus had "symptomatic HIV infection." 100 (33%) had symptomless lymphadenopathy and 16 (5%) were HIV seropositive without clinical or physical findings. Almost all patients received antiretroviral drugs as they became available. Some had minimally effective single or two drug regimens until the introduction of the protease inhibitors. Many of these regimens eventually failed and multidrug resistance, as defined by genotypic analysis developed.

Prophylaxis for *P. carinii* infection was given for $CD4^+$ T cell counts <280–300/cu mm; trimethoprim-sulfamethoxazole was most common, then dapsone-pyrimethamine, and (<2%) aerosolized pentamidine. *M. avium* complex (MAC) prophylaxis started at $CD4^+$ T cell counts <75–100, unless infection was suspected. This reduced the risk of OI relative to the investigation by Siegal et al., 1986, J. Clin. Invest. 78:115–123 in which only approximately 60% received *Pneumocystis carinii* pneumonia (PCP), and none, MAC prophylaxis.

Patients were followed serially, typically every three months, or depending upon clinical judgment. HIV load, T cell subsets and IFN-α generation were usually done together. Subjects with $CD4^+$ cell counts under 100 were monitored with blood cultures for MAC and serum cryptococcal antigen.

Healthy volunteers (n=257, 710 data points) determined the reference range for IFN-α generation.

IFN-α Generation:

Blood mononuclear cells (MNC), isolated on Ficoll/Hypaque, were cultured overnight with UV-irradiated HSV in microwells (Siegal et al, 1994, Leukemia 8:1474–1479). Supernatants were assayed for IFN using human foreskin fibroblasts as target cells challenged with vesicular stomatitis virus (Siegal et al, 1994, Leukemia 8:1474–1479). The assay sensitivity was usually 2–25 IU/ml. Concentrations below detectable limits were calculated as one unit below the limit of detection.

Virus Load:

EDTA-plasma samples were separated, frozen within 3 hours and submitted to commercial laboratories (usually Specialty Laboratories, Santa Monica, Calif.) for quantitative RT-PCR (Roche Amplicor). Ten triplicate plasma specimens at different disease stages were studied blinded by Specialty Laboratories (courtesy of T. Robins, J. S. Sevall). Mean log virus loads for these were 2.86–5.22, SEMs for individuals between 0.11–0.02, or 0.4–4% of the log virus load. The lower limit of detectibility during this study was generally 400 copies/mL. Virus loads <400 were calculated as 399 copies/mL, and considered to represent "full suppression" of viremia.

T cell Analysis:

T cell subsets were defined by a CDC-certified laboratory via flow cytometry; absolute $CD3^+CD4^+$ lymphocyte ($CD4^+$ T cell) counts were calculated from automated complete blood counts (CBC) and differential counts (System 9020, Serono-Baker, Inc).

Statistical Analysis:

Q&A version 4.0 (Symantek, Inc.) and SPSS for Windows version 5.0.2 (SPSS Inc., Chicago, Ill.) were used for statistical analysis. Student's t-test for paired or unpaired samples were used for comparison of means and routine statistics; Chi-square, Pearson's and other related nonparametric statistics were employed for correlating clinical outcomes and measures of immune reconstitution. Scatter plots, regression lines with 95% confidence limits and coefficients of correlation were generated by SPSS for Windows.

8.2. Results

IFN-α Generation, $CD4^+$ T Cell Counts & Viral Burden:

1506 determinations of virus load, 1827 of IFN-α generation and 1844 $CD4^+$ T cell counts in the 294 subjects (mean 5.1 determinations per patient, range 1–20) are summarized in FIGS. 4A and 4B. The pooled data is from multiple but different numbers of determinations on individual subjects, some of whom progressed through more than one clinical stage. To analyze bias introduced by multiple determinations, several selection criteria (Table 1) were used to generate alternative regression lines and R values. The slopes and their 95% confidence intervals in the different analyses were indistinguishable.

Although $CD4^+$ T cell counts are standard surrogates for disease status, there is striking scatter in these data. Similar scattering is seen for IFN-α generation. The correlation coefficients (for log IFN-a generation, R=−0.4277, n=1497, p<0.0005; for log CD4 count, R=−0.4982, n=1312, p<0.0005) and the regression line slopes are similar (−0.239 for log IFN-α generation, −0.250 for log CD4 count, Table 1). The slope equivalencies with respect to viral burden suggests the two cell types may be similarly responsive to changes in viral load, or directly linked biologically.

Reconstitution of IFN-α Generation & CD4+ T Cell Counts During Therapeutic Suppression of Plasma Viremia:

Recovery of $CD4^+$ T cells and IFN-α generation occurred at comparable rates following periods of viral suppression in 31 of the 82 AIDS/OI patients (FIGS. 5A and 5B). As previously shown (Siegal et al, 1986, J. Clin. Invest. 78:115–123), such patients had generally have dual deficits while still viremic ($\geq$400 copies/mL).

In the study by Siegal et al, 1986, J. Clin. Invest. 78:115–123, no subject developed OI within four months of IFN-α generation $\geq$300 IU/mL, or $CD4^+$ T cells $\geq$250/cu mm. These values are here used to define "immune reconstitution." We also re-analyzed the original data in Siegal et al, 1986, J. Clin. Invest. 78:115–123, selecting the currently widely accepted value of 200 $CD4^+$ T cells. Seventeen percent of patients with $CD4^+$ T cells counts $\geq$200/cu mm developed an OI. The corresponding 17% protective level for IFN-α generation in the same re-analysis was 150 IU/ml.

At the time of last detectable viremia (month zero in FIG. 5), the geometric means for $CD4^+$ T cells and IFN-α generation were below the critical values (horizontal reference lines). The regression line for IFN-α generation crosses the 300 IU/ml (log 2.477) reference line defining immune reconstitution at 4.0 months (95% confidence interval, 1.0 to 6.3 mos), while that for CD4+ T cell counts crosses the 250/cu mm (log 2.398) at 10.3 months (95% confidence interval 8.1 to 14.5 months). Similar analysis of the data using the 200/cu mm cutoff for CD4+ T cell counts, and the corresponding protective cutoff for IFN-α generation (150 IU/ml) indicated similar earlier recovery of IFN production.

Thus, IFN-α generation during viral suppression to levels associated with OI avoidance predates the development of protective levels of CD4+ T cells by around 6.3 months (95% confidence interval ~3.7–9.6 months). The same regression analysis was applied to 68 patients with symptomatic HIV infection with fully suppressible viremia. In this larger (and less compromised) group, the geometric mean IFN-α generation reached protective levels at 2.8 months (CI, 0.4–4.5 mos), while CD4 counts did so by 10.0 mos (CI, 8.4–13.0 mos). Selection of only two, rather than all available data points for each study subject whose viremia was suppressed (Table 2) resulted in overlapping, statistically indistinguishable slopes for recovery of the two immune parameters.

Among patients with AIDS/OI who were initially below, but later attained either or both of the cutoff values, whether they had full viral suppression or not, 26/38 (68%) attained recovery of IFN-α generation before CD4 cells. Both recovered simultaneously in 9/38 and CD4 counts recovered earlier in 3/38. Overall, IFN-α generation recovery preceded that for CD4 cells by a mean of 5.3 months (95% CI, 4.3–6.5 months).

Comparability of data from the current study and the prior analysis: Log IFN-α generation by normals in the study by Siegal et al. (1986, J. Clin. Invest. 78:115–123) was 3.25±1.25 (mean ±2 SD), in the current study, 3.26±0.92 (p=NS), indicating identity of the responses of the normals to the differing stimulation with HSV (see the Materials & Methods).

AIDS/OI subjects at their highest viremia (log viral burden 5.17±0.878 copies/ml [mean ±1 SD, n=75]), should reflect the natural history of HIV infection. They generated 2.01±0.70 log IU (mean ±1 SD) IFN-α, while the patients studied during 1981–84, before antiretroviral drugs and virus load measurement (Siegal et al., 1986, J. Clin. Invest. 78:115–123) generated 1.72±0.52 log IU (p=NS). CD4 counts under the same conditions for patients in this study were 99±123/cu mm (mean ±1 SD), and in the earlier study, were 187±208/cu mm (p=NS), indicating the similarity of the two groups of AIDS/OI patients.

Clinical Outcomes and Recovery of IFN-α Generation:

Only 26 of the 82 AIDS/OI patients maintained full viral suppression until the study's end (Table 3). Forty-two did not regenerate critical levels for either IFN-α generation or CD4+ T cells. Deaths from OI, and ongoing or newly developing OI, were restricted to these 42. Of the remaining 40, 15 achieved only the ability to generate IFN at ≧300 IU/mL (FIG. 6A), 3 had CD4 counts surpassing 250/cu mm, but made sub-critical levels of IFN, and 22 recovered both. The association of OI avoidance with immune reconstitution, as herein defined, appears to be significant (Chi-square p=0.00008). Of three patients with viral suppression to below detectability for 5–11 months, but without reconstitution of either critical function, one developed recurrent disseminated MAC infection (FIG. 6B), and another died of P. carinii pneumonia six months after the last detectable viremia. The 17 patients who had sufficient immune functioning despite remaining viremic avoided OI or OI-associated deaths, as did those with full viral suppression and reconstitution of both IFN-α generation and CD4+ T cells. The causes of non-OI-related death are listed in the footnote, Table 3. Thus, OIs and OI-related deaths occurred only when neither IFN-α generation nor CD4 counts had been reconstituted to protective levels.

8.3. Discussion

Studies characterizing immune defects in AIDS have shown abnormalities in virtually all aspects of the immune system (Pallela et al., 1998, N. Eng. J. Med. 338:853–860; Mocroft et al., 1998, Lancet 352:1725–1730; Autran et al., 1997, Science 277:112–116; Pakker et al, 1998, Nat. Med. 4:208–214; Powderly et al., 1998, J. Amer. Med. Assoc. 280:72–77; Lederman et al., 1998, J. Inf. Dis. 178:70–79; Komanduri et al., 1998, Nat. Med. 4:953–956; Kostense et al., 1998, AIDS 12:F235–240; Ledergerber et al., 1999, J. Amer. Med. Assn. 282:2220–2226; Schneider et al., 1999, Lancet 353:201–203; and Pontesilli et al., 1999, Immunol. Lett. 66:213–217). Although the dysfunction of the cells producing IFN was shown to rapidly progress over the course of HIV infection and was closely tied to the development of OI and early death (Lopez et al., 1983, J. Inf. Dis. 148:962–966 and Siegal et al., 1986, J. Clin. Invest. 78:115–123), the role of cells producing IFN in cellular immunity was undefined.

The results described herein quantify the inverse relationship of IFN-α generation to HIV burden, and demonstrate the rate at which IFN-α generation recovers under effective HIV suppression. IFN-α generation bears essentially the same relationship to plasma viremia as does the CD4+ T cell count, even though the cells in question are distinct. This similarity could be attributed either to the direct effects of HIV on two independent cells, or to a biological interaction between them in vivo.

During suppression of HIV, IFN-α generation reaches levels associated with OI resistance several months, on average, prior to re-establishment of protective levels of CD4+ T cells. This difference remains regardless of the threshold values selected, since the slopes of recovery for the two are indistinguishable.

Restoration of critical levels of either IFN-α generation or CD4+ T cell numbers (the former most often) appears to be sufficient, even in the face of ongoing viremia, to confer resistance to OI. Only infrequently (in 3/82 with AIDS/OI) was full viral suppression achieved without regeneration of either immune function, and 2/3 developed OI despite full viral suppression. Thus, adequate IFN generation is an important component of cellular immunity.

While monocytes also make IFN-a in response to certain stimuli, their response to HSV, the stimulus employed in these studies, is relatively minuscule (Feldman et al., 1994, Virology 204:1–7; Howell et al., 1994, Clin. Immunol. Immunopathol. 71:223–230; and Siegal et al., 1994, Leukemia 8:1474–1479), declines only very late in HIV infection and is not associated with susceptibility to OI (Ferbas et al., 1995, Clin. Diagn. Lab. Immunol. 2:138–142; and Feldman et al., 1995, J. Leuk. Biol. 57:214–220).

The IFN-α generation in response to HSV (Lopez et al., 183, J. Inf. Dis. 148:962–966; Siegal et al., 1986, J. Clin. Invest. 78:115–123; Kirchner et al., 1979, Immunobiology 156:65–75; Peter et al., 1980, Eur. J. Immunol. 10:547–555; Abb et al., 1983, Clin. Exp. Immunol. 52:179–184; Perussia et al., 1985, Nat. Immun. Cell. Growth Reg. 4:120–137; Bandhopadhyay et al., 1986, J. Exp. Med. 164:180–195; Fitzgerald-Bocarsly et al., 1988, J. Leuk. Biol. 43:323–334; Chehimi et al., 1989, Immunology 68:488–490; Rappocciolo et al, 1989, J. Clin. Microbiol. 27:41–48; Feldman et al., J. Interferon Res. 10:435–446; Sandberg et al., 1990, J. Immunol. 145:1015–1020; Sandberg et al., 1991, Scand. J. Immunol. 34:565–576; Cederblad et al., 1991, Scand. J. Immunol. 34:549–555; Starr et al., 1993, Adv. Exp. Med. Biol. 329:173–178; Fitzgerald-Bocarsly et al., 1993, Pharmacol. Therapeut. 60:39–62; Ferbas et al., 1994, J. Immunol. 152:4649–4662; Feldman et al., 1994, Virology 204: 1–7; Howell et al., 1994, Clin. Immunol. Immunopathol. 71:223–230; Ferbas et al., 1995, Clin. Dign. Lab. Immunol. 2:138–142; Feldman et al., 1995, J. Leuk. Biol. 57:214–220; Svensson et al., 1996, Scand. J. Immunol. 44:164–172; Svensson et al., 1996, J. Interferon Cytok. Res. 16:7–16; Ghanekar et al., 1996, J. Immunol. 157:4028–4036; Payvandi et al., 1998, J. Immunol. 160:5861–5868; and Milone et al., 1998, J. Immunol. 161:2391–2399) has recently been shown to derive from unique plasmacytoid cells found blood and in T cell areas of lymphoid tissue (Siegal et al., 1999, Science 284:1835–1837). These interferon-producing cells (IPC) metamorphose into type-2 dendritic cells (DC2) following exposure to IL-3 and CD40 ligand (Grouard et al., 1997, J. Exp. Med. 185:1101–1111). Mature DC2 have been reported to foster Th2-type immune responses (Rissoan et al., 1999, Science 283:1183–1186). However, IPC functional integrity is associated clinically with protection from infection by intracellular pathogens, implicating these cells in Th1-type immune responses. In other disorders associated with OI (hairy cell leukemia, steroid therapy, certain cases of idiopathic CD4 lymphopenia, common variable immunodeficiency and immunodeficiency with thymoma), IFN-α generation is compromised (M Shodell, FP Siegal: abstract submitted, FASEB AAI/CIS Congress, Seattle, Wash., May, 2000), again indicating a role for IPCs in cellular immunity.

Thus, at least under certain circumstances, IPCs may foster Th1 immunity, a type of immune response lost progressively during HIV infection (Clerici et al., 1994, Immunol. Today 15:575–581; Empson et al., 1999, J. All. Clin. Immunol. 103:833–842; Leigh et al., 1998, J. Acquir. Immune Def. Syndr. Hum. Retrovirol. 19:373–380; and Harrison et al., 1997, J. Immunol. 158:459–463). IFN-α has recently been shown to bias immature human T cells towards the Th-1 pathway (Brinkman et al., J. Exp. Med. 178:1655–1663; and Parronchi et al., 1996, Eur. J. Immunol. 26:697–703; and Rogge et al., 1998, J. Immunol. 161: 6567–6574), leading to enhanced IFN-γ and IL-2 production, both directly and by up-regulating the expression of IL-12 receptors, features characteristic of the Th1 response. IPCs are uniquely specialized to produce IFN-α after microbial stimuli (Siegal et al., 1999, Science 284:1835–1837), and are also strategically located in T cell areas of lymphoid tissue. IPC may thus initiate the development of Th1 immunity in normal humans, locally providing the type-1 IFNs that both directly enhance IFN-γ production and increase the receptiveness of immature T (Th-0) cells to subsequent contact with IL-12, delivered by DC1. The next IPC developmental stage, the type 2 dendritic cell (DC2), has been shown to foster development of Th-2-type responses, which in turn can down-regulate Th-1 (Rissoan et al., 1999, Science 283:1183–1186).

The absence of IFN-α signaling in lymphoid tissue suggests the functional loss of IPCs in late-stage HIV infection, which may reduce any residual biasing towards Th1. Regeneration of IFN-α during HIV therapy, months before recovery of $CD4^+$ T cell numbers, suggests the regeneration of IPCs, which can enhance cellular (Th1) immunity.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

TABLE 1

Relationship of HIV Burden to IFN-α generation or $CD4^+$ T cell counts

| CONDITIONS ANALYSED | PARAMETER | SLOPE OF REGRESSION LINE (95% CONFIDENCE INTERVAL) | CORRELATION COEFFICIENT (R) |
|---|---|---|---|
| All subjects, all data points | IFN-α generation | −0.239 (−0.264 to −0.213) | 0.428 |
| | $CD4^+$ T cell counts | −0.250 (−0.274 to −0.227) | 0.498 |
| All subjects, first and last time studied | IFN-α generation | −0.233 (−0.281 to −0.184) | 0.414 |
| | $CD4^+$ T cell counts | −0.268 (−0.310 to −0.226) | 0.516 |
| All subjects with OI, all points while still viremic | IFN-α generation | −0.337 (−0.416 to −0.259) | 0.417 |
| | $CD4^+$ T cell counts | −0.239 (−0.318 to −0.160) | 0.327 |
| All subjects with OI, at highest viral burden | IFN-α generation | −0.385 (−0.547 to −0.224) | 0.486 |
| | $CD4^+$ T cell counts | −0.247 (−0.402 to −0.092) | 0.356 |
| All symptomatic subjects who were suppressed, T = 0 and T = last* | IFN-α generation | −0.215 (−0.281 to −0.150) | 0.387 |
| | $CD4^+$ T cell counts | −0.171 (−0.225 to −0.117) | 0.401 |

*"T = 0" is date of last detectable viremia before suppression to below limit of detectability, 400 copies/ml; "T = last" is last time point at which viremia was still suppressed (see FIG. 5 legend).

TABLE 2

Reconstitution of IFN-α generation or $CD4^+$ T cell counts after suppression of HIV viremia

| CONDITIONS OF ANALYSIS | PARAMETER | SLOPE OF REGRESSION LINE (95% CONFIDENCE INTERVAL) | CORRELATION COEFFICIENT (R) |
|---|---|---|---|
| All subjects with OI, all available data | IFN-α generation | 0.0419 (0.0231 to 0.0607) | 0.375 |
| | $CD4^+$ T cell counts | 0.0429 (0.0267 to 0.0591) | 0.453 |
| All subjects with OI, T = 0 and T = last* | IFN-α generation | 0.0538 (0.0290 to 0.0786) | 0.499 |
| | $CD4^+$ T cell counts | 0.0507 (0.0250 to 0.0763) | 0.484 |

TABLE 2-continued

Reconstitution of IFN-α generation or CD4+ T cell counts after suppression of HIV viremia

| CONDITIONS OF ANALYSIS | PARAMETER | SLOPE OF REGRESSION LINE (95% CONFIDENCE INTERVAL) | CORRELATION COEFFICIENT (R) |
|---|---|---|---|
| All symptomatic subjects, T = 0 and T = last* | IFN-α generation CD4+ T cell counts | 0.0298 (0.0199 to 0.0398) 0.0219 (0.0133 to 0.0306) | 0.352 0.328 |

*"T = 0" is date of last detectable viremia before suppression to below limit of detectability, 400 copies/ml; "T = last" is last time point at which viremia was still suppressed (see FIG. 5 legend).

TABLE 3

Relationship of clinical status to level of viremia and immune reconstitution for 82 patients having a diagnosis of AIDS/OI and treated with antiretroviral drugs.

| Viral suppression | Immune reconstitution* | No OI | OI | Dead of OI or (Other Causes)** | Total |
|---|---|---|---|---|---|
| >400 copies | neither IFN, CD4 | 11 | 10 | 16 (2) | 39 |
| <400 copies | neither IFN, CD4 | 1 | 1 | 1 (0) | 3 |
| >400 copies | either or both | 15 | 0 | 0 (2) | 17 |
| <400 copies | either or both | 22 | 0 | 0 (1) | 23 |

*Ability to generate ≥ 300 IU IFN, a CD4+T cell count ≥ 250/cu mm, or both prior to assessment of health status

**Non-OI deaths included: hepatoma, pulmonary embolism, AIDS dementia complex, CNS lymphoma, lung carcinoma

| Chi-square | value | DF | p |
|---|---|---|---|
| Pearson | 36.216 | 10 | 0.00008 |

What is claimed is:

1. A method of monitoring the progression of HIV infection or AIDS in a patient, the method comprising:
   (a) measuring the number of pDC2 cells in a lymphoid tissue or blood sample obtained from the patient, wherein the pDC2 cells are $CD4^+$, $CD3^-$ and $CD11c^-$; and
   (b) comparing the number of pDC2 cells in said sample with the number of pDC2 cells in a control sample, where the control sample is from a subject or subjects free of HIV infection or AIDS,
   wherein a number of pDC2 cells in the patient sample below the number of pDC2 cells in the control sample indicates that HIV infection or AIDS is progressing.

2. A method of assessing the effectiveness of a therapeutic or pharmaceutical composition in treating, inhibiting or ameliorating HIV infection or AIDS in a patient, the method comprising measuring and comparing the number of pDC2 cells in a lymphoid tissue or blood sample obtained from the subject before and after treatment with the therapeutic or pharmaceutical composition, wherein the pDC2 cells are $CD4^+$, $CD3^-$ and $CD11c^-$, and wherein an increase in the number of pDC2 cells in the sample after treatment indicates that the composition is effective.

3. The method of claim 1, wherein the sample is a peripheral blood sample.

4. The method of claim 1, wherein the pDC2 cell number is determined by counting $CD4^+$ $CD3^-$ $CD11c^-$ cells.

5. The method of claim 4, wherein the pDC2 cells are isolated before counting.

6. The method of claim 5, wherein the pDC2 cells are isolated by magnetic-bead depletion of B, T and natural killer (NK) cells and monocytes, followed by fluorescence activated cell sorting.

7. The method of claim 2, wherein the blood sample is a peripheral blood sample.

8. The method of claim 2, wherein the pDC2 cell number is determined by counting $CD4^+$ $CD3^-$ $CD11c^-$ cells.

9. The method of claim 8, wherein the pDC2 cells are isolated before counting.

10. The method of claim 9, wherein the pDC2 cells are isolated by magnetic-bead depletion of B, T and natural killer (NK) cells and monocytes, followed by fluorescence activated cell sorting.

11. A method of monitoring the progression of HIV infection or AIDS in a patient, the method comprising:
    (a) measuring the number of pDC2 cells in a lymphoid tissue or blood sample obtained from the patient, wherein the pDC2 cells are $CD4^+$, $CD3^-$ and $CD11c^-$; and
    (b) comparing the number of pDC2 cells in said sample with the number of pDC2 cells in a control sample, where the control sample is from a subject or subjects having HIV infection or AIDS that is progressing,
    wherein a number of pDC2 cells in the patient sample above the number of pDC2 cells in the control sample indicates that HIV infection or AIDS is not progressing.

12. The method of claim 11, wherein the sample is a peripheral blood sample.

13. The method of claim 11, wherein the pDC2 cell number is determined by counting $CD4^+$ $CD3^-$ $CD11c^-$ cells.

14. The method of claim 13, wherein the pDC2 cells are isolated before counting.

15. The method of claim 13, wherein the pDC2 cells are isolated by magnetic-bead depletion of B, T and natural killer (NK) cells and monocytes, followed by fluorescence activated cell sorting.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gatggccgtg ctggtgctca                                       20

<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
tgatttctgc tctgacaacc tccc                                  24

```
<210> SEQ ID NO 3
<211> LENGTH: 30
<212> TYPE: DNA
<213> ORGANISM: Artificial
<220> FEATURE:
<223> OTHER INFORMATION: probe

<400> SEQUENCE: 3
ctcaagccat ctctgtcctc catgagatga                                    30

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ttgaatggga ggcttgaata                                               20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ctatggtcca ggcacagtga                                               20

<210> SEQ ID NO 6
<211> LENGTH: 30
<212> TYPE: DNA
<213> ORGANISM: Artificial
<220> FEATURE:
<223> OTHER INFORMATION: probe

<400> SEQUENCE: 6
ggctggaatg agactattgt tgagaacctc                                    30

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
ggcagaccga gatgaatcct ca                                            22

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
caggtccagg ggtcttggtc c                                             21
```